(12) United States Patent
Adamko et al.

(10) Patent No.: US 9,050,313 B2
(45) Date of Patent: Jun. 9, 2015

(54) ACTIVATION OF INNATE AND ADAPTIVE IMMUNE RESPONSES BY A GINSENG EXTRACT

(71) Applicant: VALEANT CANADA LP, Laval (CA)

(72) Inventors: Darryl J. Adamko, Edmonton (CA); Kenneth L. Rosenthal, Hamilton (CA); Jacqueline Shan, Edmonton (CA); Yingqi Wu, Edmonton (CA); Sharla Sutherland, Edmonton (CA)

(73) Assignee: VALEANT CANADA LP (CA)

( * ) Notice: Subject to any disclaimer, the term of this patent is extended or adjusted under 35 U.S.C. 154(b) by 7 days.

(21) Appl. No.: 13/846,267

(22) Filed: Mar. 18, 2013

(65) Prior Publication Data

US 2013/0295205 A1    Nov. 7, 2013

Related U.S. Application Data

(63) Continuation of application No. 12/919,941, filed as application No. PCT/IB2009/000379 on Feb. 27, 2009, now abandoned.

(60) Provisional application No. 61/064,354, filed on Feb. 29, 2008.

(51) Int. Cl.
*A61K 36/258*    (2006.01)
*A61K 36/25*    (2006.01)

(52) U.S. Cl.
CPC ............... *A61K 36/258* (2013.01); *A61K 36/25* (2013.01)

(58) Field of Classification Search
USPC ........................................................ 424/728
IPC .................................................. A61K 36/258
See application file for complete search history.

(56) References Cited

U.S. PATENT DOCUMENTS

| 4,469,685 | A | 9/1984 | Kojima et al. | |
|---|---|---|---|---|
| 5,318,906 | A | 6/1994 | Sakata et al. | |
| 6,083,932 | A | 7/2000 | Pang et al. | |
| 6,156,291 | A | 12/2000 | Pang et al. | |
| 6,432,454 | B1 | 8/2002 | Shan et al. | |
| 6,555,527 | B1 | 4/2003 | Yun et al. | |
| 7,067,160 | B2 * | 6/2006 | Shan et al. | 424/728 |
| 7,186,423 | B2 * | 3/2007 | Shan et al. | 424/728 |
| 7,413,756 | B2 * | 8/2008 | Shan et al. | 424/728 |
| 7,901,716 | B2 | 3/2011 | Kwak et al. | |
| 8,309,075 | B2 * | 11/2012 | Albers et al. | 424/93.45 |
| 2003/0124207 | A1 | 7/2003 | Shan et al. | |
| 2004/0137087 | A1 | 7/2004 | Shan et al. | |
| 2005/0287230 | A1 | 12/2005 | Young | |
| 2006/0034951 | A1 * | 2/2006 | Kwak et al. | 424/728 |
| 2009/0047405 | A1 | 2/2009 | Zhang | |

FOREIGN PATENT DOCUMENTS

| CN | 1088448 A | 6/1994 |
|---|---|---|
| EP | 1037645 | 12/2006 |
| JP | S61-18722 | 1/1986 |
| JP | S63-239229 | 10/1988 |
| JP | 02-045499 | 2/1990 |
| JP | H02-45501 | 2/1990 |
| JP | 2002-17299 | 1/2002 |
| RU | 1410322 | 3/1996 |
| WO | 87/05936 | 10/1987 |
| WO | 99/30725 | 6/1999 |
| WO | WO99/30725 | 6/1999 |
| WO | 00/50054 | 8/2000 |
| WO | 03/060467 | 7/2003 |
| WO | WO03/086438 | 10/2003 |

OTHER PUBLICATIONS

Anonymous: "News Release: McGill University Pre-Clinical Research Demonstrates Positive Results for CVT-E002 in Cancer Model" Internet Article, [Online] May 24, 2006.
Chiscon, M.Q. and E.S. Golub (1972) Functional development of the interacting cells of the immune response. I. Development of T cell and B cell function. J Immunol. 108:1379-1386.
Database WPI, Section CH, Week 199533, Derwent Publications.
Fujimoto Y. et al: "Cytotoxic Acetylenes from Panax Quinquefolium" Chemical and Pharmaceutical bulletin, Pharmaceutical Society of Japan, Tokyo, JP, vol. 39, No. 2, Feb. 1991, pp. 521-523.
Nolan, V., M. Lipoldova and A. Zajicova (1991) Immunological nonreactivity of newborn mice: Immaturity of T cells and selective action of neonatal suppressor cells. Cell Immunol. 137:216-223.
Klinman, N.R. (1976) The acquisition of B cell competence and diversity. Am J Pathol. 85:693-703.

(Continued)

*Primary Examiner* — Chris R Tate
(74) *Attorney, Agent, or Firm* — Quarles & Brady LLP

(57) ABSTRACT

The invention is directed to ginseng fractions and methods for activating innate and adaptive immune responses to prevent, treat or ameliorate a condition in a subject by administering to the subject an effective amount of a ginseng fraction, a pharmaceutical composition comprising the fraction in combination with another medicament or with one or more pharmaceutically acceptable carriers, or a food item comprising the fraction. The fraction may be made from *Panax quinquefolius* or may be selected from CVT-E002, $PQ_2$, $PQ_{223}$ and purified fractions from CVT-E002, $PQ_2$, and $PQ_{223}$.

10 Claims, 20 Drawing Sheets

(56) References Cited

OTHER PUBLICATIONS

Liu et al., Yaoxue Xuebao, vol. 23, No. 11, p. 863-867 (1988). (English Abstract on last page).
McElhaney et al., J. Alternative Complementary Med. 2006. vol. 12, No. 2, pp. 153-157.
Sherwin, W.K. and D.T. Rowlands. (1975) Determinants of the hierarchy of humoral immune responsiveness during ontogeny. J Immunol. 115:1549-1554.
Spear, P.G. and G. Edelman. (1974) Maturation of the humoral immune response in mice. J Exp Med. 139:249-263.
Spear, P.G., A.L. Wang, U. Rutishauser, et al. (1973) Characteristics of splenic lymphoid cells in fetal and newborn mice. J Exp Med. 138:557-573.
Strober, S. (1984) Natural suppressor (NS) cells, neonatal tolerance and total lymphoid irradiation: exploring obscure relationships. Ann Rev Immunol. 2:219-237.
Sun et al., Planta Med., vol. 56, No. 5, pp. 445-448 (1992).
Sun, L.Z-Y., N.L. Currier and S.C. Miller. (1999) The American Coneflower: A prophylactic role involving nonspecific immunity. J Alt Comp Med. 5(5):437-446.
Yamada et al., Phytother, Res., vol. 9, No. 4, pp. 264-269 (1995).
Zhou Yu et al., Biosciences Information Service, Philadelphia, PA, vol. 23, No. 9, pp. 551-552, 577 (1998) (Abstract).
CV Technologies Inc. News Release entitled "Cold-fx Sets Record Straight: Health Canada's Approval of New Medical Claims Unchanged; lower dosage for long-term or immediate symptom relief approved first, Company now pursuing higher short-term dosage with strong basis for approval". Mar. 5, 2007. 5 pages.
Good Morning America Internet Article entitled "Fighting the Common Cold". Oct. 25, 2005. 4 pages. Obtained from http://abcnews.go.com/GMA/Flu/story?id=1247773.
Restriction Requirement for U.S. Appl. No. 12/600,301 dated May 16, 2012.
Office Action for New Zealand Application No. 587615 dated Jun. 22, 2012.
Office Action for U.S. Appl. No. 12/600,301 dated Jul. 12, 2012.
Office Action for Chinese Application No. 200980114017.7 dated Jul. 13, 2012.
Office Action for Australian Patent Application No. 2009219793 dated Jul. 30, 2012.
Restriction Requirement for U.S. Appl. No. 12/919,941 dated Sep. 20, 2012.
Restriction Requirement for U.S. Appl. No. 13/294,043 dated Nov. 27, 2012.
Office Action issued for U.S. Appl. No. 12/919,941 dated Nov. 28, 2012.
Final Office Action issued on U.S. Appl. No. 13/294,043 dated Feb. 7, 2013.
Office Action issued for Japanese Application No. 2010-548206 dated Apr. 24, 2013.
Office Action for European Application No. 09716101.2 dated Jun. 20, 2013.
Office Action for Chinese Application No. 200980114017.7 dated Dec. 19, 2012.
Final Office Action issued on U.S. Appl. No. 12/600,301 dated Nov. 5, 2012.
Stein, D., Roth, S., Vogelsang, E., and Nusslein-Volhard, C., The polarity of the dorsoventral axis in the *Drosophila* embryo is defined by an extracellular signal. Cell 65 (1991) 725-735.
Takeda, K., Kaisho, T., and Akira, S., Toll-like receptors. Annu.Rev. Immunol. 21 (2003) 335-376.
Takeuchi, O., Hoshino, K., Kawai, T., Sanjo, H., Takada, H., Ogawa, T., Takeda, K., and Akira, S., Differential roles of TLR2 and TLR4 in recognition of gram-negative and gram-positive bacterial cell wall components. Immunity. 11 (1999) 443-451.
Wang, M., Guilbert, L. J., Li, J., Wu, Y., Pang, P., Basu, T. K., and Shan, J. J., A proprietary extract from North American ginseng (*Panax quinquefolium*) enhances IL-2 and IFN-gamma productions in murine spleen cells induced by Con-A. Int.Immunopharmacol. 4 (2004) 311-315.
Wang, M., Guilbert, L. J., Ling, L., Li, J., Wu, Y., Xu, S., Pang, P., and Shan, J. J., Immunomodulating activity of CVT-E002, a proprietary extract from North American ginseng (*Panax quinquefolium*). J.Pharm.Pharmacol. 53 (2001) 1515-1523.
Yao, X. D. and Rosenthal, K. L., Herpes simplex virus type 2 virion host shutoff protein suppresses innate dsRNA anti-viral pathways in human vaginal epithelial cells. J.Gen.Virol. (2011).
Yao, X. D., Fernandez, S., Kelly, M. M., Kaushic, C., and Rosenthal, K. L., Expression of Toll-like receptors in murine vaginal epithelium is affected by the estrous cycle and stromal cells. J. Reprod. Immunol. 75 (2007) 106-119.
Yarovinsky, F., et al. TLR11 activation of dendritic cells by a protozoan profilin-like protein. Science 308 (2005) 1626-1629.
Zhang, D., Zhang, G., Hayden, M. S., Greenblatt, M. B., Bussey, C., Flavell, R. A., and Ghosh, S., A toll-like receptor that prevents infection by uropathogenic bacteria. Science 303 (2004) 1522-1526.
Olivenstein, et al., Airway Hyperresponsiveness, Clinical Respiratory Physiology, Chapter 62, pp. 709-720.
Akira, S. and Takeda, K., Toll-like receptor signalling. Nat. Rev. Immunol. 4 (2004) 499-511.
Akira, S., Uematsu, S., and Takeuchi, 0., Pathogen recognition and innate immunity. Cell124 (2006) 783-801.
Alexopoulou, L., Holt, A. C., Medzhitov, R., and Flavell, R. A., Recognition of double-stranded 3 RNA and activation of NF-kappaB by Toll-like receptor 3. Nature 413 (2001) 732-738.
Ashkar, A. A. and Rosenthal, K. L., Toll-like receptor 9, CpG DNA and innate immunity. Curr. Mol. Med. 2 (2002) 545-556.
Ashkar, A. A., Bauer, S., Mitchell, W. J., Vieira, J., and Rosenthal, K. L., Local delivery of CpG oligodeoxynucleotides 4 induces rapid changes in the genital mucosa and inhibits replication, but not entry, of herpes simplex virus type 2. J. Virol. 77 (2003) 8948-8956.
Ashkar, A. A., Yao, X. D., Gill, N., Sajic, D., Patrick, A. J., and Rosenthal, K. L., Toll-like receptor (TLR)-3, but not TLR4, agonist protects against genital herpes infection in the absence of inflammation seen with CpG DNA. J.Infect. D Dis. 190 (2004) 1841-1849.
Barrett, B. and Brown, D., Therapeutic Monograph for CVT-E002 (Cold-fx), American Botanical Council, abc. D herbalgram.org/site/DocServer/ColdFX_TheraMONO.pdf? . . . 842.
Barton, G. M., Kagan, J. C., and Medzhitov, R., Intracellular localization of Toll-like receptor 9 prevents recognition of D self DNA but facilitates access to viral DNA. Nat.Immunol. 7 (2006) 49-56.
Bauer, M., Redecke, V., Ellwart, J. W., Scherer, B., Kremer, J. P., Wagner, H., and Lipford, G.B., Bacterial CpG-DNA triggers activation and maturation of human CD11c-, CD123+ dendritic cells. J.Immunol. 166 (2001) 5000-5007.
Coban, C., et al. Toll-like receptor 9 mediates innate immune activation by the malaria pigment hemozoin. J.Exp.Med. 201 (2005) 19-25.
CV Technologies Inc. News Release entitled "Cold-fX Sets Record Straight: Health Canada's Approval of New Medical Claims v Unchanged; lower dosage for long-term or immediate symptom relief approved first, Company now pursing higher short-term dosage with strong basis for approval". Mar. 5, 2007. 5 pages.
Diebold, S. S., Kaisho, T., Hemmi, H., Akira, S., and Reise Sousa, Innate antiviral responses by means of TLR7-mediated recognition of single-stranded RNA. Science 303 (2004) 1529-1531.
Dumais, N., Patrick, A., Moss, R. B., Davis, H. L., and Rosenthal, K. L., Mucosal immunization with inactivated human immunodeficiency virus plus CpG oligodeoxynucleotides induces genital immune responses and protection against intravaginal challenge. J.Infect.Dis. 186 (2002) 1098-1105.
European Search Report and Written Opinion dated Feb. 23, 2012 for PCT/IB2009000379.
Gallichan, W. S., Woolstencroft, R.N., Guarasci, T., McCiuskie, M. J., Davis, H. L., and Rosenthal, K. L., Intranasal immunization with CpG oligodeoxynucleotides as an adjuvant dramatically increases IgA and protection against herpes simplex virus-2 in the genital tract. J.Immunol. 166 (2001) 3451-3457.

(56) References Cited

OTHER PUBLICATIONS

Gantner, B. N., Simmons, R. M., Canavera, S. J., Akira, S., and Underhill, D. M., Collaborative induction of inflammatory responses by dectin-1 and Toll-like receptor 2. J.Exp.Med. 197 (2003) 1107-1117.

Good Morning America Internet Article entitled "Fighting the Common Cold". Oct. 25, 2005. 4 pages. Obtained from http://abcnews.go.com/GMA/Fiu/story?id= 124 7773.

Hargreaves, D. C. and Medzhitov, R., Innate sensors of microbial infection. J. Clin. Immunol. 25 (2005) 503-510.

Hayashi, F., Smith, K. D., Ozinsky, A., Hawn, T. R., Yi, E. C., Goodlett, D. R., Eng, J. K., Akira, S., Underhill, D. M., and Aderem, A., The innate immune response to bacterial flagellin is mediated by Toll-like receptor 5. Nature 410 (2001) 1099-1103.

Heil, F., Hemmi, H., Hochrein, H., Ampenberger, F., Kirschning, C., Akira, S., Lipford, G., Wagner, H., and Bauer, S., Species-specific recognition of single-stranded RNA via toll-like receptor 7 and 8. Science 303 (2004) 1526-1529.

Hemmi, H., Kaisho, T., Takeuchi, 0., Sato, S., Sanjo, H., Hoshino, K., Horiuchi, T., Tomizawa, H., Takeda, K., and Akira, S., Small antiviral compounds activate immune cells via the TLR7 MyD88-dependent signaling pathway. Nat. Immunol. 3 (2002) 196-200.

International Search Report and Written Opinion for International Application No. PCT/182009/000379—EP1037645.

Iwasaki, A. and Medzhitov, R., Toll-like receptor control of the adaptive immune responses. Nat. Immunol. 5 (2004) 987-995.

Janeway, C. A., Jr. and Medzhitov, R., Introduction: the role of innate immunity in the adaptive immune response. D Semin.Immunol. 10 (1998) 349-350.

Janeway, C. A., Jr. and Medzhitov, R., Lipoproteins take their toll on the host. Curr.Biol. 9 (1999) R879-R882.

Janeway, C. A., Jr., The immune system evolved to discriminate infectious nonself from noninfectious self. Immunol. Today 13 (1992) 11-16.

Jiang, J. Q., Patrick, A., Moss, R. B., and Rosenthal, K. L., CDS+ T-cell-mediated cross-clade protection in the genital tract following intranasal immunization with inactivated human immunodeficiency virus antigen plus CpG oligodeoxynucleotides. J.Virol. 79 (2005) 393-400.

Jing, Y ., et al. A proprietary extract of *Panax quinquefolius* I(.;V r-E002) strmulates inflammatory cytokine secretion from monocytes and augments IFN-gamma secretion from NK cells in response to influenza virus stimulation. (Submitted). (2006) Not Published—Please note the following monograph references this study and summarizes the results of the study: Barret, B., Brown, D., Therapeutic Monograph for CVT-E002 (COLDfX), American Botanical Council.

Jurk, M. Heil, F. Vollmer, J., Schetter, C., Krieg, A. M., Wagner, H., Lipford, G., and Bauer, S., Human TLR7 or TLR8 independently confer responsiveness to the antiviral compound R-848. Nat. Immunol. 3 (2002) 499.

Kawai, T. and Akira, S., Innate immune recognition of viral infection. Nat. Immunol. 7 (2006) 26 131-137.

Kawai, T. and Akira, S., Pathogen recognition with Toll-like receptors. Curr.Opin.Immunol. 17 (2005) 338-344.

Krug, A. et al., Toll-like receptor expression reveals CpG DNA as a unique microbial stimulus for plasmacytoid dendritic cells which synergizes with CD40 ligand to induce high amounts of IL-12. Eur. J .Immunol. 31 (2001) 3026-3037.

Kwant, A. and Rosenthal, K. L., Intravaginal immunization with viral subunit protein plus CpG oligodeoxynucleotides induces immunity protective immunity against HSV-2. Vaccine 22 (2004) D 3098-3104.

Latz, E., et al. TLR9 signals after translocating from the ER to CpG DNA in the lysosome. Nat. Immunol. 5 (2004) 190-198.

Lemaitre, B., et al. The dorsoventral regulatory gene cassette spatzle/Tolllcactus controls the potent antifungal response in *Drosophila* adults. Cell 86 (1996) 973-983.

Matsumoto, M., Funami, K., Tanabe, M., Oshiumi, H., Shingai, M., Seto, Y., Yamamoto, A., and Seya, T., Subcellular localization of T oil-like receptor 3 in human dendritic cells. J. Immunol. 171 (2003) 3154-3162.

McElhaney et al.,Efficacy of COLD-fX in the Prevention of Respiratory Symptoms in Community-Dwelling Adults: A Randomized, Double-Blinded, Placebo Controlled Trial, J. Alternative Complementary Med. 2006. vol. 12, No. 2, pp. 153-157.

McElhaney, J. E., et al. A placebo-controlled trial of a proprietary extract of North American ginseng (CVT-E002) to prevent acute respiratory illness in institutionalized older adults. J. Am. Geriatr. Soc. 52 (2004) 13-19.

Medzhitov, R., Preston-Hurlburt, P., and Janeway, C. A., Jr., A human homologue of the *Drosophila* Toll protein signals activation of adaptive immunity. Nature 388 (1997) 394-397.

Miller, S. C., The role of phytocompounds in immunoenhancement and cancer abatement (2006).

Office Action issued Mar. 9, 2011 for New Zealand Patent Application No. 587615.

Office Action issued Oct. 12, 2011 for Mexican Patent Application No. MX/a/2010/009479.

Office Action issued Sep. 21, 2011 for Chinese Patent Application No. 200980114017.7—CN1285752 cited in Office Action—corresponds to W099/30725.

O'Neill, L.A., How Toll-like receptors signal: what we know and what we don't know. Curr.Opin.Immunol. 18 (2006) 3-9.

Philpott, D. J. and Girardin, S. E., The role of Toll-like receptors and Nod proteins in bacterial infection. Mol. Immunol. 41 (2004) 1099-1108.

Poltorak, A., et al. Defective LPS signaling in C3H/HeJ and 37 C57BU1 OScCr mice: mutations in Tlr4 D gene. Science 282 (1998) 2085-2088.

Predy, G. N., Goel, V., Lovlin, R. E., and Basu, T. K., Immune modulating effects of daily supplementation of COLD-fX D (a proprietary extract of North American ginseng) in healthy adults. J. Clin. Biochem. Nutr. 39 (2006) 162-167.

Predy, G. N., Goel, V., Lovlin, R., Donner, A., Stitt, L., and Basu, T. K., Efficacy of an extract of North American ginseng containing poly-furanosyl-pyranosyl-saccharides for preventing upper respiratory tract infections: a randomized controlled trial. CMAJ. 173 (2005) 1043-1048.

Roach, J. C., Glusman, G., Rowen, L., Kaur, A., Purcell, M. K., Smith, K. D., Hood, L. E., and Aderem, A., The evolution of vertebrate Toll-like receptors. Proc.Nati.Acad.Sci.U.S.A 102 (2005) 9577-9582.

Seth, R. B., Sun, L., and Chen, Z. J., Antiviral innate immunity pathways. Cell Res. 16 (2006) 141-147.

\* cited by examiner

FIG. 5

ACTIVATION OF INNATE AND ADAPTIVE IMMUNE RESPONSES BY A GINSENG EXTRACT

FIELD OF THE INVENTION

This invention relates to ginseng fractions and methods for activating innate and adaptive immune responses to prevent, treat or ameliorate a condition in a subject by administering to the subject an effective amount of a ginseng fraction, a pharmaceutical composition or food item comprising the fraction. Such conditions include allergies, asthma, viral and microbial infections, and cancer. The ginseng fractions may be used as vaccine adjuvants.

BACKGROUND

A proprietary water soluble extract from the roots of North American ginseng (*Panax quinquefolium*), CVT-E002, is commercially available as COLD-FX™. This extract differs from other Asian or American ginseng products in the content of polysaccharides and ginsenosides, primarily consisting of poly-furanosyl-pyranosyl-saccharides. Batch-to-batch quality of the product is certified by ChemBioPrint™ technology, which assures its chemical as well as pharmacological consistency. This proprietary natural extract is known to have immunomodulatory effects (Wang et al. 2001, 2004). CVT-E002 enhances the proliferation of mouse spleen cells, and increases production of interleukin-1 (IL-1), IL-6, tumor necrosis factor (TNF)-α and nitric oxide (NO) from peritoneal macrophages in vitro. Administration of CVT-E002 to mice increased serum immunoglobulin G (IgG) antibody levels (Wang et al., 2001) and daily dosing of CVT-E002 to mice with viral-induced leukemia increased the proportions of macrophages and NK cells in the bone marrow and spleen while reducing the leukemic cell numbers (Miller, 2006). In a recent study on human peripheral blood mononuclear cells (PBMC) cultured with live influenza virus, CVT-E002 was effective in enhancing the production of IL-2 and interferon γ (IFNγ) (Jing et al., submitted). IL-2 and IFNγ are major T and NK cell cytokines and are associated with virus-specific adaptive immune responses. In a clinical study, daily low dose supplementation of COLD-FX™ to healthy adults increased the proportion of NK cells in plasma (Predy et al., 2006).

Being the first line of defense against microbial pathogens, both macrophages and NK cells are important components of innate immunity. These cells act immediately to limit proliferation and spread of infectious agents through release of antimicrobial agents such as cytokines, interferons and chemokines and by their phagocytic or cytolytic activities.

Since pre-clinical studies suggested potential use of CVT-E002 for the prophylaxis of virus-related upper respiratory infections, a clinical trial involving 198 institutionalized seniors was conducted. This study demonstrated that daily administration of CVT-E002 for 4 months during an influenza season reduced relative risk of acute respiratory illness due to influenza and respiratory syncytial virus by up to 89% (McElhaney et al., 2004). Another study also showed CVT-E002 significantly reduced the recurrence of respiratory infections in 323 healthy middle-aged adults (Predy et al., 2005). CVT-E002 treatment also reduced the severity and duration of symptoms related to upper respiratory tract infections in healthy adults. In a randomized double-blind, placebo controlled trial of 43 community-dwelling adults aged 65 or older, daily ingestion of CVT-E002 reduced the relative risk and duration of respiratory symptoms by 48% and 55%, respectively. Daily CVT-E002 administration was shown to be a safe, natural therapeutic means of prevention of acute respiratory illness in healthy seniors.

The mammalian immune system has evolved multiple, layered and interactive defensive systems to protect against infections, which have been broadly divided into innate immunity and adaptive immunity. Innate immunity is the first line of defense against microbial pathogens and acts almost immediately to limit early proliferation and spread of infectious agents through activation of phagocytic and antigen-presenting cells, such as dendritic cells and macrophages, and initiation of inflammatory responses through the release of a variety of cytokines, chemokines and anti-microbial factors, such as interferons and defensins. Innate immunity is evolutionarily ancient and for many years its study was largely ignored by immunologists as relatively non-specific. For the most part, humans are protected against infection by the innate immune system. If infectious organisms penetrate innate immune defenses, the innate defenses facilitate and guide the generation of adaptive immune responses that are directed against highly specific determinants that are uniquely expressed by the invading pathogen. These responses are dependent on rearrangement of specific antigen-receptor genes in B-cells and T-cells and result in production of high-affinity antigen-specific antibodies (humoral immunity) and T-cells or cell-mediated immunity. Antibodies facilitate removal, destruction or neutralization of extracellular pathogens and their toxins. T-cell-mediated immune responses help eliminate or control intracellular pathogens. In contrast to innate immune responses, adaptive immune responses have the hallmark of specific immune memory.

Previous studies have attempted to determine how the host innate immune system detects infection and how it discriminates between self and pathogens or infectious non-self. The discovery and characterization of Toll-like receptors (TLRs) have provided great insight into innate immune recognition and established a key role of the innate immune system in host defense against infection (Akira et al., 2006; Hargreaves and Medzhitov, 2005; Kawai and Akira, 2006; Philpott and Girardin, 2004; Seth et al., 2006). TLRs are key molecules in innate and adaptive immunity. The innate immune system uses multiple families of germline-encoded pattern recognition receptors (PRRs) to detect infection and trigger a variety of anti-microbial defense mechanisms (Janeway and Medzhitov, 1998). These PRRs are evolutionarily highly conserved among species from plants and fruit flies to mammals. The strategy of innate immune recognition is based on the detection of highly conserved and essential structures present in many types of microorganisms and absent from host cells (Janeway, 1992; Janeway and Medzhitov, 1999). Since the targets of innate immune recognition are conserved molecular patterns, they are called pathogen-associated molecular patterns (PAMPs). PAMPS have important features that make them ideal targets for innate immune sensing. PAMPs are produced only by microorganisms and not by host cells. This is the basis for discrimination of self and infectious non-self. PAMPs are conserved between microorganisms of a given class, allowing a limited number of PRRs to detect the presence of a large class of invading pathogens. For example, a pattern in LPS allows a single PRR to detect the presence of any Gram-negative bacteria. PAMPs are essential for microbial survival and any mutation or loss of PAMPs is either lethal for the organism or greatly reduces their adaptive fitness. These new insights into innate immune recognition are revolutionizing the understanding of immune defense, pathogenesis, and treatment and prevention of infectious diseases.

TLRs represent one family of PRRs that are evolutionarily conserved transmembrane receptors that detect PAMPs and function as signaling receptors. TLRs were discovered in *Drosophila* where they play a role in development of the fruit flies ventral/dorsal orientation (Stein et al., 1991). When this gene was mutated, the flies that developed were found to be "toll" which is German slang for crazy or "far out." Further, flies with mutation of Tolls were found to be highly susceptible to fungal infections (Lemaitre at al., 1996). To date, 11 TLRs have been identified in mammals, each sensing a different set of microbial stimuli and activating distinct signaling pathways and transcription factors that drive specific responses against the pathogens (Kawai and Akira, 2005). TLRs are type I integral membrane glycoproteins characterized by extracellular domains containing various numbers of leucine-rich-repeat (LRR) motifs, a transmembrane domain and a cytoplasmic signaling domain homologous to that of the interleukin-1 receptor (IL-1R), termed the Toll/IL-1R homology (UR) domain (O'Neill, 2006). The LRR domains are composed of 19-25 tandem LRR motifs, each of which is 24-29 amino acids in length.

TLR4, the first mammalian TLR discovered, proved to be the long sought receptor for Gram-negative bacterial lipopolysaccharide (LPS) (Medzhitov et al., 1997; Poltorak et al., 1998). TLR2 recognizes peptidoglycan, in addition to the lipoproteins and lipopeptides of Gram-positive bacteria and mycoplasma (Takeda et al., 2003; Takeuchi et al., 1999). TLR2 can form heterodimers with TLR1 or TLR6 to discriminate between diacyl and triacyl lipopeptides, respectively (Takeda et al., 2003). Further, TLR2 in collaboration with the non-TLR receptor dectin-1 mediates the response to zymosan, found in the yeast cell-wall (Gantner et al., 2003). TLR5 recognizes flagellin, a protein component of bacterial flagella (Hayashi et al., 2001). TLR11, a close relative of TLR5, was found to be abundantly expressed in the urogenital tract of mice and was associated with protection against uropathogenic bacteria (Zhang et al., 2004), and was recently shown to recognize profilin-like protein from the protozoan parasite *Toxoplasma gondii* (Yarovinsky et al., 2005). TLR3, 7, 8 and 9 recognize nucleic acids and are not expressed on the cell surface, but are exclusively expressed in endosomal compartments (Latz et al, 2004; Matsumoto et al., 2003). TLR3 is involved in recognition of double-stranded RNA (dsRNA) generated during viral infection (Alexopoulou et al., 2001), whereas closely related TLR 7 and 8 recognize viral single stranded (ss)RNA rich in guanosine or uridine (Diebold at al., 2004; Heil at al, 2004) and synthetic imidazoquinoline-like molecules, imiquimod and resiquimod (R-848) (Hemmi at al., 2002; Jurk et al., 2002). TLR9 mediates the recognition of bacterial and viral unmethylated CpG DNA motifs (Hemmi et al., 2000) and was recently also shown to recognize non-DNA pathogenic components, such as hemozoin from malarial parasites (Coban et al., 2005). TLR10 plays a role in the pathogen-mediated inflammation pathway, pathogen recognition and activation of innate immunity, but the TLR10 ligand is presently unknown.

TLRs can also be divided into six major subfamilies based on sequence similarity (Roach et al., 2005), each recognizing related PAMPS. The subfamily consisting of TLR1, TLR2 and TLR6 recognizes lipopeptides, TLR3 recognizes dsRNA, TLR4 LPS, TLR5 flagellin, and the TLR9 subfamily that includes highly related TLR7 and TLR8 recognize nucleic acids. Importantly, the subcellular localization of TLRs correlates with the nature of their ligands, rather then sequence similarity (Hargreaves and Medzhitov, 2005). TLR1, 2, 4, 5, 6 and 10 are present on the surface plasma membrane where they are involved in the pathogen mediated inflammation pathway and/or recognize bacterial and viral components, while antiviral TLRs, TLR3, 7, 8, and 9 are expressed in intracellular endosomes. Since nucleic acids recognized by antiviral TLRs are also found in vertebrates, their location in endosomes limits their reactivity to self nucleic acids (Barton et al., 2006). TLR11 is present on the cell surface and is a receptor for uropathogenic bacteria and protozoan parasites.

Signaling by TLRs is complex and has been reviewed elsewhere (Akira and Takeda, 2004; O'Neill, 2006). Briefly, all TLRs with the exception of TLR3 signal through the adaptor molecule myeloid differentiation factor 88 (MyD88), a cytoplasmic protein containing a TIR domain and a death domain. Ultimately, NF-κB and MAPKs are activated downstream of TRAF6 leading to production of proinflammatory cytokines and chemokines, such as TNF-α, IL-6, IL-1β and IL-12. In addition to MyD88, TLR3 and TLR4 signal through TRIF, another TIR-containing adaptor that is required for production of type I interferons and type I interferon-dependent genes.

TLRs are expressed on a variety of immune and non-immune cells. Murine macrophages express TLR1-9, reflecting their importance in the initiation of proinflammatory responses. Plasmacytoid DCs (pDCs) that produce large amounts of type I interferons during viral infections express TLR7 and 9. All conventional DCs in the mouse express TLR1, 2, 4, 6, 8 and 9, while TLR3 is confined to the CD8+ and CD4− CD8− DC subset (Iwasaki and Medzhitov, 2004). In humans, TLR9 expression is restricted to pDCs and B-cells (Bauer et al., 2001; Krug et al., 2001).

There is great interest in understanding expression of TLRs on mucosal epithelial cells (ECs) that serve as the first line of defense against most infections. In our recent studies (Yao X-D et al., 2007), we have concentrated on understanding expression and regulation of TLRs on ECs in the genital tract of mice and humans. Laser capture microdissection (LCM) was used to show that the estrous cycle in female mice profoundly influences expression of TLRs in the vaginal epithelium. mRNA expression of essentially all TLRs except TLR11 were significantly increased during diestrus and especially following treatment with the long acting progestin Depo-Provera (Yao X-D et al., manuscript submitted). These findings contribute to our understanding of innate immune defense against sexually-transmitted infections, and enhance the quality of female reproductive health.

Mucosal delivery of TLR ligands, including CpG oligodeoxynucleotides (ODN which is a ligand for TLR9), dsRNA, and flagellin, can induce an innate anti-viral effect that can protect mice against intravaginal (IVAG) challenge with HSV-2 (Ashkar and Rosenthal, 2002). Studies have showed that intranasal administration of purified envelope glycoprotein (gB) from HSV-2 plus CpG ODN as an adjuvant induced strong gB-specific IgA and IgG in the vaginal tract (persisting throughout the estrous cycle) as well as systemic and genital gB-specific CTL, and protected against lethal IVAG HSV-2 infection (Gallichan et al., 2001). Subsequently, it was shown that intranasal immunization with inactivated gp120-depleted HIV-1 plus CpG ODN induced anti-HIV IgA in the genital tract and HIV-specific T-cell-mediated immune responses, including production of IFNγ and β-chemokines (Dumais et al., 2002). Further, mice immunized intranasally with HIV-1 plus CpG induced CD8+ T-cells in the genital tract, providing cross-clade protection against IVAG challenge with recombinant vaccinia viruses expressing HIV-1 gag from different clades (Jiang et al., 2005). More recently, although the genital tract has been considered to be a poor immune inductive site, especially following immunization with non-replicating antigens, intravaginal (IVAG) immunization of female mice with recombinant subunit HSV-2 gB plus CpG induced higher levels of gB-specific IgG and IgA antibodies in serum and vaginal washes versus mice immunized with antigen alone and mice immunized with gB plus CpG were better protected against vaginal infection with HSV-2 (Kwant and Rosenthal, 2004). Thus, it is possible to induce protective immune responses following IVAG immunization with a non-replicating subunit protein antigen provided an appropriate mucosal adjuvant is used.

Recent studies have shown that PAMPs including CpG DNA, dsRNA, and LPS were capable of inhibiting herpes simplex virus type 2 (HSV-2) and vesicular stomatitis virus (VSV) in vitro (Ashkar et al., 2003 & 2004). A single dose of CpG ODN delivered transmucosally to the vaginal mucosa, in the absence of any viral antigen, protected against genital infection with lethal doses of HSV-2. This protection was mediated by the innate immune system, since it occurred in knockout mice lacking B and T cells. Local IVAG delivery of CpG ODN resulted in rapid proliferation and thickening of the vaginal epithelium and induction of a TLR-9-dependent antiviral state that did not block virus entry but inhibited viral replication in vaginal epithelial cells (Ashkar et al., 2003). Mucosal delivery of dsRNA, the ligand for TLR3, protected against genital HSV-2 infection without the local or systemic inflammation seen with CpG ODN (Ashkar et al., 2004). Therefore, local delivery of TLR3 ligand may be a safer means of protecting against genital viral infection.

TLRs induce a range of responses depending on the cell type in which they are activated (Ashkar and Rosenthal, 2002; Iwasaki and Medzhitov, 2004). For example, treatment of DCs with CpG DNA that acts through TLR9 activates the DCs to mature, including upregulation of MHC class II and costimulatory molecules, as well as production of proinflammatory cytokines, chemokines and enhancement of antigen presentation. Similarly, treatment of B-cells with CpG induces their activation and proliferation, secretion of antibody as well as IL-6 and IL-10 and the B-cells become resistant to apoptosis. Activation of immune cells via CpG DNA induces a Th1-dominated response.

The mechanisms by which PRRs mediate host defense against pathogens are the focus of intense research. Due to their ability to enhance innate immune responses, there is a need for novel strategies to use ligands, synthetic agonists or antagonists of PRRs (i.e., "innate immunologicals") as stand alone agents to provide protection or treatment against infection with intracellular bacteria, parasites and viruses. Further, activation of innate immune system through PRRs using their respective ligands or agonists represents a strategy to enhance immune responses against specific pathogens, making agents which signal via PRRs potential vaccine adjuvants.

There is a need for a natural, herbal fraction or composition which specifically activates the innate and adaptive immune responses to treat associated conditions such as allergies, asthma, viral and microbial infections, and cancer without causing deleterious side effects or discomfort. The types of immune responses are well known. Th1 responses are characterized by the generation of killer T cells and certain antibodies in response to intracellular pathogens and intracellular defects such as cancers. Th2 responses fight extracellular pathogens. Allergic reactions occur in response to environmental substances (i.e., allergens), and are the result of specific Th2 responses. Th2 responses are characterized by the generation of other specific types of antibodies and are typical of allergic reactions, in which an allergen is mistaken for a pathogen on a mucosal surface and triggers an immune response resulting in symptoms such as watery eyes, airway inflammation and contraction of airway muscle cells in the lungs. TLR activation induces antigen-presenting cells to produce cytokines that favor Th1-type immune responses, thereby preventing or reducing the development of deleterious Th2 responses due to exposure to allergens.

Allergies are specifically characterized by excessive activation of white blood cells called mast cells and basophils by IgE, resulting in an extreme inflammatory response. When an allergy-prone person is initially exposed to an allergen, large amounts of the corresponding, specific IgE antibody are made. The IgE molecules attach to the surface of mast cells (in tissue) or basophils (in the circulation). Mast cells are found in the lungs, skin, tongue, and linings of the nose and intestinal tract. When an IgE antibody on a mast cell or basophil encounters its specific allergen, the IgE antibody signals the mast cell or basophil to release chemicals such as histamine, heparin, and substances that activate blood platelets and attract secondary cells such as eosinophils and neutrophils. The activated mast cell or basophil also synthesizes new mediators, including prostaglandins and leukotrienes. These chemical mediators cause the symptoms associated with allergies, including wheezing, sneezing, runny eyes and itching. Common allergic reactions include eczema, hives, hay fever, asthma, food allergies, and reactions to the venom of stinging insects such as wasps and bees.

An asthma exacerbation is a serious deterioration in the lung function of a patient often resulting in hospitalization and even death. Asthma occurs when the main air passages of the lungs, the bronchial tubes, become inflamed. The muscles of the bronchial walls tighten, and cells in the lungs produce extra mucus further narrowing the airways, causing minor wheezing to severe difficulty in breathing. Asthma is often triggered by a respiratory viral infection, such as the common cold, but other irritants such as cigarette smoke, dust mites, animal dander, plant pollen, air pollution, deodorants and perfume can make asthma symptoms more frequent, severe, and uncontrollable. Other asthma triggers include, exercise, cold air, and emotional stress. The majority of asthma exacerbations are precipitated by common airway virus infections. In children, being atopic and having a virus infection are both major risk factors for being admitted to a hospital for a wheezing illness. While the clinical importance of asthma attacks and specifically viral exacerbation of asthma is clear, the reasons why patients with asthma become so ill after common cold viruses remains poorly understood.

Normally, viral infections cause an influx of neutrophils into the airways with a large mononuclear cell component of predominantly CD8+ T-cells. However, it has become apparent that viral infections can produce a range of inflammatory responses, including airway eosinophilia, depending on the pre-existing condition of the host. In atopic individuals, experimental rhinovirus infection increases the recruitment of eosinophils to the airways after antigen challenge and causes increased airway reactivity compared to non-allergic individuals. After intranasal infection with rhinovirus, biopsies of the lower airways of asthmatic individuals contain increased eosinophils, which persist even into convalescence. In patients with asthma, the presence of airway eosinophils during periods of exacerbations has been well established. The finding of eosinophils in airway during asthma exacerbation becomes somewhat paradoxical, considering that these exacerbations are often triggered by viral infection. While the association of eosinophils and their degranulation products in the airways has been described during virus infection in patients with asthma, whether eosinophils are active in response to the virus and how this activation might occur is unknown.

For an asthma exacerbation to occur, the current understanding suggests that effector cells (i.e. eosinophils, mast cells, basophils, neutrophils) may be activated. FIG. 1 illustrates a model of virus-induced eosinophil mediator release in the airway which results in airway hyperreactivity via dysfunction of the neural control of airway smooth muscle. Virus or virus antigen is presented to memory T-cells. Activated T-cells (CD4) release an unknown soluble degranulation factor, likely a cytokine such as GM-CSF. These T-cells may also express cell surface ligands, for example, ICAM-1. Eosinophils respond to the soluble mediator, cell surface ligands, or combination thereof with release of various eosinophil mediators (i.e. eosinophil major basic protein, eosinophil peroxidase, RANTES).

In asthmatics, virus-induced eosinophil mediator release in the airways correlates with the development of asthma exacerbation. For the eosinophil to be involved in the development of virus-induced asthma exacerbations, it must respond to the virus either indirectly via another cell or directly. This process would represent virus-induced eosinophil mediator release.

Western physicians have been reluctant to prescribe herbal medicines due to lack of scientific research of their preventative and therapeutic properties. However, herbal medicines do not require the lengthy development time and high costs normally encountered with synthetic drugs. Further, they are readily available and offer the subject a more comfortable and affordable alternative with minimal side effects compared to prescription medication or vaccines.

SUMMARY OF THE INVENTION

In one embodiment, the present invention is directed to a method of treating a condition susceptible to treatment by activation of innate immunity signaling in a subject in need of such treatment, comprising administering to the subject an effective amount of at least one ginseng fraction. In one embodiment, the condition is selected from an allergy, asthma, viral infection, microbial infection or cancer. In one embodiment, the viral infection is from a respiratory or mucosally transmitted virus including, but not limited to, influenza, corona virus, herpes, respiratory syncytial virus, Rhabdoviridae, or human immunodeficiency virus.

In one embodiment, the fraction is made from a ginseng selected from *Panax quinquefolius, Panax trifolza, Panax ginseng, Panax japonicus, Panax schinseng, Panax notoginseng, Panax pseudoginseng, Panax vietnanzensis, Panax elegatior, Panax wangianus, Panax bipinratifidus*, green or fresh ginseng, white ginseng, or red ginseng. In one embodiment, the fraction is a fraction of *Panax quinquefolius*. In one embodiment, the fraction is selected from CVT-E002, $PQ_2$, $PQ_{223}$ or purified fractions from CVT-E002, $PQ_2$ and $PQ_{223}$. In one embodiment, the fraction is CVT-E002. In one embodiment, CVT-E002 modulates signal transduction from a Toll-like receptor. In one embodiment, the Toll-like receptor is Toll-like receptor 2. In one embodiment, the Toll-like receptor is a heterodimer of Toll-like receptor 2 and Toll-like receptor 6. In one embodiment, the Toll-like receptor is a heterodimer of Toll-like receptor 2 and Toll-like receptor 1. In one embodiment, the Toll-like receptor is Toll-like receptor 4. In one embodiment, CVT-E002 induces up-regulation of lymphocytes and antigen-presenting cells, cytokine secretion, secretion of anti-viral factors, or combinations thereof.

In one embodiment, the present invention is directed to a fraction of ginseng for the activation of innate and adaptive immune responses to prevent, treat or ameliorate a condition. In one embodiment, the fraction is made from a ginseng selected from *Panax quinquefolius, Panax trifolia, Panax ginseng, Panax japonicus, Panax schinseng, Panax notoginseng, Panax pseudoginseng, Panax vietnamensis, Panax elegatior, Panax wangianus, Panax bipinratifidus*, green or fresh ginseng, white ginseng, or red ginseng. In one embodiment, the fraction is a fraction of *Panax quinquefolius*. In one embodiment, the fraction is selected from CVT-E002, $PQ_2$, $PQ_{223}$ or purified fractions from CVT-E002, $PQ_2$ and $PQ_{223}$. In one embodiment, the fraction is CVT-E002.

In one embodiment, the present invention is directed to a pharmaceutical composition comprising a ginseng fraction in combination with another medicament or with one or more pharmaceutically acceptable carriers including food items for the activation of innate and adaptive immune responses to prevent, treat or ameliorate a condition. In one embodiment, the fraction is made from a ginseng selected from *Panax quinquefolius, Panax trifolia, Panax ginseng, Panax japonicus, Panax schinseng, Panax notoginseng, Panax pseudoginseng, Panax vietnanzensis, Panax elegatior, Panax wangianus, Panax bipinratifidus*, green or fresh ginseng, white ginseng, or red ginseng. In one embodiment, the fraction is a fraction of *Panax quinquefolius*. In one embodiment, the fraction is selected from CVT-E002, $PQ_2$, $PQ_{223}$ or purified fractions from CVT-E002, $PQ_2$ and $PQ_{223}$. In one embodiment, the fraction is CVT-E002.

In one embodiment, the present invention is directed to a food item comprising a ginseng fraction for the activation of innate and adaptive immune responses to prevent, treat or ameliorate a condition. In one embodiment, the fraction is made from a ginseng selected from *Panax quinquefolius, Panax trifolia, Panax ginseng, Panax japonicus, Panax schinseng, Panax notoginseng, Panax pseudoginseng, Panax vietnanzensis, Panax elegatior, Panax wangianus, Panax bipinratifidus*, green or fresh ginseng, white ginseng, or red ginseng. In one embodiment, the fraction is a fraction of *Panax quinquefolius*. In one embodiment, the fraction is selected from CVT-E002, $PQ_2$, $PQ_{223}$ or purified fractions from CVT-E002, $PQ_2$ and $PQ_{223}$. In one embodiment, the fraction is CVT-E002.

In another embodiment, the present invention is directed to use of a ginseng fraction for the preparation of a pharmaceutical composition or a food item for the activation of innate and adaptive immune responses to prevent, treat or ameliorate a condition. In one embodiment, the condition is selected from an allergy, asthma, viral infection, microbial infection or cancer. In one embodiment, the viral infection is from a respiratory or mucosally transmitted virus including influenza, corona virus, herpes, respiratory syncytial virus, Rhabdoviridae, and human immunodeficiency virus. In one embodiment, the fraction is made from a ginseng selected from *Panax quinquefolius, Panax trifolia, Panax ginseng, Panax japonicus, Panax schinseng, Panax notoginseng, Panax pseudoginseng, Panax vietnamensis, Panax elegatior, Panax wangianus, Panax bipinratifidus*, green or fresh ginseng, white ginseng, or red ginseng. In one embodiment, the fraction is a fraction of *Panax quinquefolius*. In one embodiment, the fraction is selected from CVT-E002, $PQ_2$, $PQ_{223}$ or purified fractions from CVT-E002, $PQ_2$ and $PQ_{223}$. In one embodiment, the fraction is CVT-E002.

In another embodiment, the present invention is directed to a method for activating innate and adaptive immune responses to prevent, treat or ameliorate a condition in a subject in need of such activation by administering a ginseng fraction or a pharmaceutical composition comprising the fraction in combination with another medicament or with one or more pharmaceutically acceptable carriers including food items, to the subject.

In yet another embodiment, the present invention is directed to a method for preventing, treating or ameliorating a condition associated with activation of innate immunity signaling comprising modulating signal transduction from Toll-like receptors by administering a ginseng fraction to a subject in need.

BRIEF DESCRIPTION OF THE DRAWINGS

FIG. 5 shows a table which lists cytokines/chemokines measured by ELISA/Searchlight, n=1, Arrows represent values relative to appropriate respective control.

FIG. 7A shows the subpopulations of cells. FIG. 7B shows results of screening cells for DQ-OVA uptake and degradation under different conditions. Values represent percentage of cells within each category that are DQ-OVA positive. FIG. 7C shows the evaluation of DC maturation by means of size and granularity (values represent percentage of total cells present in each category). FIG. 7D are flow cytometry images representing the subpopulations of DC without (left) and with (right) CVT-E002 treatment.

FIG. 17A shows vaginal pathology scores of C57BL/6 mice given CVT-E002, HT1001 or PBS WAG following HSV-2 IVAG challenge.

Figure 1:
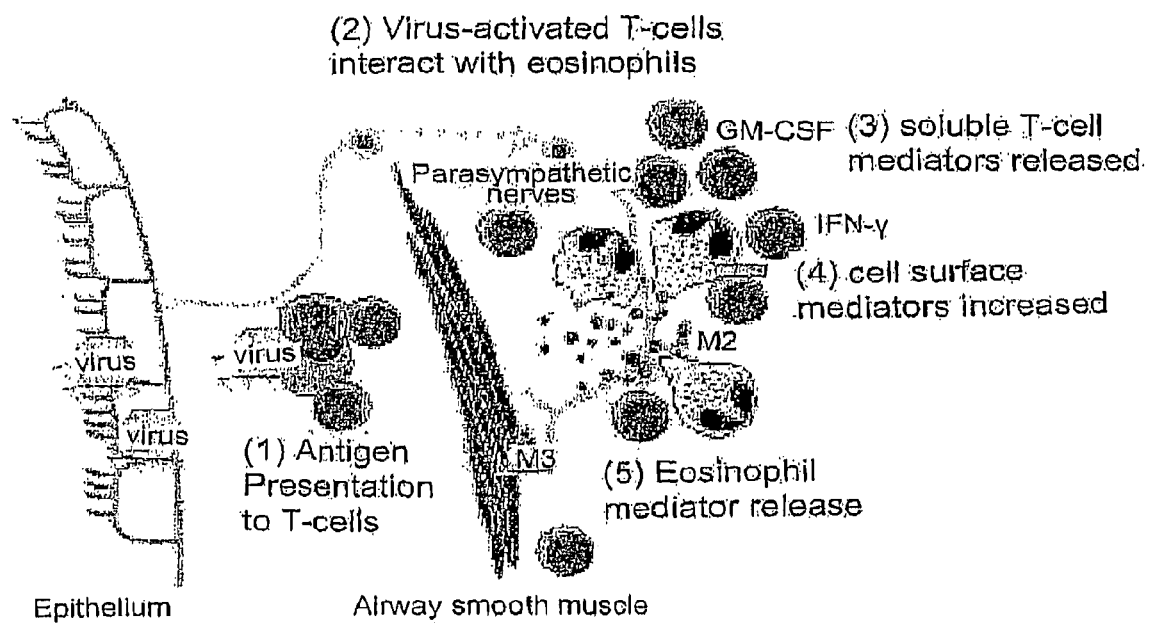
FIG. 1 shows a working model of virus-induced eosinophil mediator release in the airway.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

As used herein and in the claims, the terms and phrases set out below have the meanings which follow.

"Biocompatible" means generating no significant undesirable host response for the intended utility. Most preferably, bio compatible materials are non-toxic for the intended utility. Thus, for human utility, biocompatible is most preferably non-toxic to humans or human tissues.

"Carrier" means a suitable vehicle which is biocompatible and pharmaceutically acceptable, including for instance, one or more solid, semisolid or liquid diluents, excipients, adjuvants, flavours, or encapsulating substances which are suitable for administration.

"Subject" means humans or other vertebrates. The subject may be a child or an adult.

A "functional food" is similar in appearance to, or may be, a conventional food that is consumed as part of a usual diet, and is demonstrated to have physiological benefits and/or reduce the risk of disease beyond basic nutritional functions, i.e. they contain an active ingredient.

A "nutraceutical" is a product isolated or purified from foods that is generally sold in medicinal forms not usually associated with foods. A nutraceutical should have a physiological benefit or provide protection against disease.

A "vaccine adjuvant" means any substance or compound capable of promoting an increased or enhanced immune response when added to a vaccine.

A "vaccine" means any compound or preparation of antigens designed to stimulate a normal immune response. The vaccine may be prophylactic or therapeutic.

"Effective amount" and/or "therapeutic amount" means a dosage sufficient to provide prevention, treatment and/or amelioration of the disease state being treated. This will vary depending on the patient, the disease and the treatment being effected. For example, in the case of a viral infection, an "effective amount" is that amount necessary to substantially improve the likelihood of treating the infection, in particular that amount which improves the likelihood of successfully preventing infection or eliminating infection when it has occurred.

A "fraction" is meant to refer to a concentrated preparation obtained from extraction of a plant or plant part with a suitable solvent such as, for example, water, ethanol, a mixture thereof, oils or any other suitable solvent well known in the state of the art of plant extraction. The fraction or extract can be used as such if pharmacologically acceptable, or the solvent of the resulting solutions is removed and the residue is used as such or after further work up, for example, after resolving or re-suspending in a suitable solvent. The term "plant" is understood to mean the whole plant and plant parts comprising the active ingredients, for example, the leaves, the stems, the fruits or roots.

"Ginseng" is meant to refer to any variety and type of ginseng including, but not limited to, those listed below.

TABLE 1

Varieties and Types of Ginseng

| Latin name(s) | Common name(s) |
|---|---|
| Panax quinquefolius | North American/Canadian |
| Panax trifolia | Eastern region of North America |
| Panax ginseng | Asian ginseng |
| Panax japonicus | Korean ginseng |
| Panax schinseng | Oriental ginseng |
| Panax notoginseng | Japanese ginseng |
| Panax pseudoginseng | Chinese ginseng |
| Panax vietnamensis | Nepalese ginseng |
| Panax elegatior | Vietnamese ginseng |
| Panax wangianus | Wild ginseng |
| Panax bipinratifidus | Green or fresh ginseng |
| | Red ginseng |
| | White ginseng |
| | Xi Yang Shen |
| | Ren Shen/Gao Li Shen |
| | Tienchi/Sanchi |
| | Sâm Ngọc Linh |

It will be understood by those skilled in the art that there are many other genuses of *Panax* genus plants belonging to Araliaceae from which ginseng fractions may be obtained and used within the context of the present invention. The term "ginseng" also includes wild or processed ginseng. Wild ginseng is ginseng which has not been planted and cultivated domestically, but grows naturally and is harvested from wherever it is found to be growing. Processed ginseng includes, for example, fresh or green ginseng, white ginseng, and red ginseng. Fresh or green ginseng is raw ginseng harvested in the field. White ginseng is obtained by drying fresh ginseng, and red ginseng is obtained by steaming fresh ginseng followed by drying the steamed ginseng.

A "ginseng fraction" or "ginseng fractions" is meant to refer to fractions made from any variety and type of ginseng as listed in Table 1 or described above, and subfractions obtained from these ginseng fractions, which exhibit the activity of activating innate and adaptive immune responses to prevent, treat or ameliorate a condition in a subject, as verified by conducting one or more in vitro or in vivo pharmacological evaluations.

"CVT-E002" is meant to refer to an exemplary ginseng fraction obtained from *Panax quinquefolius*, and which has immunoregulating properties (as previously described in U.S. Pat. Nos. 6,432,454; 7,067,160; 7,186,423 and 7,413,756 which are hereby incorporated by reference). CVT-E002 exhibits the additional activity of activating innate and adaptive immune responses as described herein.

"$PQ_2$" is meant to refer to an exemplary ginseng fraction obtained from *Panax quinquefolius*, and which has immunoregulating properties as previously described in U.S. Pat. Nos. 6,432,454; 7,067,160; 7,186,423 and 7,413,756 which are hereby incorporated by reference.

"$PQ_{223}$" is meant to refer to an exemplary ginseng fraction obtained from *Panax quinquefolius*, and which has immunoregulating properties as previously described in U.S. Pat. Nos. 6,432,454; 7,067,160; 7,186,423 and 7,413,756 which are hereby incorporated by reference.

It will be appreciated by those skilled in the art that fractions from plants or plant parts other than ginseng, or synthetic fractions which may equally well be used in the present context, are within the scope of the present invention, as long as their chemical properties and activities are sufficiently similar to the ginseng fraction used herein.

The present invention relates to a ginseng fraction, or a pharmaceutical composition or food item comprising the fraction, for activating innate and adaptive immune responses to prevent, treat or ameliorate a condition. Further, the present invention relates to a ginseng fraction, or a pharmaceutical composition or food item comprising the fraction, for the activation of the innate and adaptive immune system through pattern recognition receptors (PPRs), such as the Toll-like receptors, to treat, prevent or ameliorate various conditions in a subject. Such conditions include, but are not limited to, viral and microbial infections, allergies, asthma, and cancer. To the inventors' knowledge, this is the first time that a natural plant-derived fraction has been shown to specifically activate the mammalian innate immune system via PRRs. In one embodiment, the ginseng fraction is a fraction of *Panax quinquefolius*. In one embodiment, the ginseng fraction is selected from the group consisting of CVT-E002, $PQ_2$, $PQ_{223}$ and purified fractions from CVT-E002, $PQ_2$ and $PQ_{223}$. In one embodiment, the ginseng fraction is CVT-E002.

The ginseng fraction is typically prepared by first drying and powderizing the ginseng plant or plant parts and then performing an extraction process using an appropriate solvent, typically water, ethanol, ethanol/water mixture, methanol, butanol, iso-butanol, acetone, hexane, petroleum ether or other organic solvents. The fraction or extract may then be further evaporated and thus concentrated to yield a dried extract by means of spray drying, vacuum oven drying, or freeze-drying. Processes for making exemplary ginseng fractions selected from the group consisting of CVT-E002, $PQ_2$, $PQ_{223}$ and purified fractions from CVT-E002, $PQ_2$ and $PQ_{223}$, from a water soluble extract of the root portion of *Panax quinquefolius* have previously been described in U.S. Pat. Nos. 6,432,454; 7,067,160; 7,186,423 and 7,413,756, the disclosures of which are hereby incorporated by reference.

Once prepared, the ginseng fraction is evaluated to assess and confirm the activity of activating innate and adaptive immune responses by conducting one or more in vitro or in vivo pharmacological evaluations. In the present invention, such evaluations include, but are not limited to, an in vitro study of the effects of an exemplary ginseng fraction, CVT-E002, on virus replication (see Examples 1 and 2) and dendritic cell function (see Example 3). For the present invention, any pharmacological evaluations are suitable, provided they are focused upon indication of the above activities in either the ginseng fraction, a representative sample from a batch of the ginseng fraction in the event of large scale manufacturing, or a subfraction of the ginseng fraction. Batch-to-batch quality of the product may be certified by ChemBioPrint™ Technology, which assures its chemical as well as pharmacological consistency, as described in U.S. Pat. No. 6,156,291 which is hereby incorporated by reference.

Further, the present invention is directed to the use of the ginseng fraction alone or in combination with another medicament, in the preparation of a pharmaceutical composition or a food item suitable for activating innate and adaptive immune responses to treat, prevent or ameliorate a condition in a subject. In one embodiment, the ginseng fraction is a fraction of *Panax quinquefolius*. In one embodiment, the ginseng fraction is selected from the group consisting of CVT-E002, $PQ_2$, $PQ_{223}$ and purified fractions from CVT-E002, $PQ_2$ and $PQ_{223}$. In one embodiment, the ginseng fraction is CVT-E002.

Further, the present invention is directed to a pharmaceutical composition comprising the ginseng fraction in combination with a pharmaceutically acceptable carrier. Those skilled in the art are familiar with any pharmaceutically acceptable carrier that would be useful in this regard, and therefore the procedure for making pharmaceutical compositions in accordance with the invention will not be discussed in detail. Suitably, the pharmaceutical compositions may be in the form of tablets, capsules, liquids, lozenges, lotions, aerosol, solutions suitable for injection or suppositories.

The oral compositions can include an inert diluent or an edible carrier. For the purpose of oral therapeutic administration, the ginseng fraction can be incorporated with excipients and used in the form of tablets, troches, or capsules, e.g., gelatin capsules. Oral compositions can also be prepared using a fluid carrier for use as a mouthwash. Pharmaceutically compatible binding agents or other carrier materials can be included as part of the composition. Such binding agents and carriers can be a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art. Transmucosal administration can be accomplished through the use of nasal sprays, suppositories or retention enemas for rectal delivery. The suppositories can include conventional suppository bases such as cocoa butter and other glycerides. For transdermal administration, the active compounds are formulated into ointments, salves, gels, or creams as generally known in the art.

The ginseng fraction can also be prepared with carriers that will protect the active agents against rapid elimination from the body, such as a controlled release formulation, including implants, coatings and microencapsulated delivery systems.

The ginseng fraction may be used alone or in combination with another medicament. The ginseng fractions of the invention are especially suitable for co-administration with a chemotherapeutic agent or as a supplement to radiation therapy, since cancer patients are known to have serious suppression of the immune system. The ginseng fractions may also be used as immunomodulators or vaccine adjuvants.

Diverse solid, semi-solid or liquid food items may be prepared to include the ginseng fraction as an active ingredient. Non-limiting examples of such food items include cereal, pasta, confectionery products (for example, cookies, cakes, caramels, gum, hard candies), nutrition, snack or meal replacement bars, yogurt, gelatin, jam, puddings, soups, a base of fruits or vegetables, beverages (for example, juices, soft drinks, sports energy drinks, bottled water, milk, soy products), and child and infant foods (for example, infant formulas, modified milk powder, baby food). Further, the ginseng fraction may be used an active ingredient in functional foods, nutraceuticals, or dietary supplements.

Formulations of the ginseng fraction may lose some activity with aging and are thus either prepared in stable forms, or prepared fresh for administration, for example in multicomponent kit form so as to avoid aging and to maximize the effectiveness of the ginseng fraction. Suitable kits or containers are well known for maintaining the phases of formulations separate until the time of use. For instance, a kit containing the ginseng fraction in powder form may be packaged separately from a sterile carrier such as saline solution, alcohol or water, and possibly other ingredients in dosage specific amounts for mixing at the time of use. The ginseng fraction may be provided in a "tea bag"-type infuser, pouch or sachet, for generating liquid formulations at the time of use. The tea bag-type infuser is advantageous in that the pouch may serve as a filter for small particulates of the powder that may be detrimental with certain types of administration (for example, via injection or infusion). Particulates may also be removed by for example, filtration.

Dosages of ginseng fractions in accordance with the invention depend upon the particular condition to be treated, as well as the age, sex and general health condition of the patient. However, suitable dosages may be found in the range between 1 and 5000 mg/kg body weight per day, with between 1 and 10 daily doses. The preferred dosage is 400 mg daily for chronic or preventive use. For acute uses, significantly higher doses are initially administered. For example, 1800 mg could be administered on the first day divided into three doses, 1200 mg could be administered on the second day divided into three doses and 900 mg could administered on the third day divided into three doses. Thereafter, 200-400 mg could be administered daily until the symptoms are reduced. The ginseng fractions may be administered orally, via injection or infusion, topically, nasally, occularly, vaginally or rectally.

The ginseng fraction of this invention is effective in the activation of innate and adaptive immune responses to prevent, treat or ameliorate various conditions in a subject. Additionally, since the ginseng fraction is prepared from a natural, edible product, the potential for side effects is decreased. The ability of a ginseng fraction to stimulate innate and adaptive immune responses to prevent, treat or ameliorate viral infection, allergy and asthma is discussed below and/or demonstrated in the Examples using an exemplary ginseng fraction, CVT-E002.

Figure 8A:
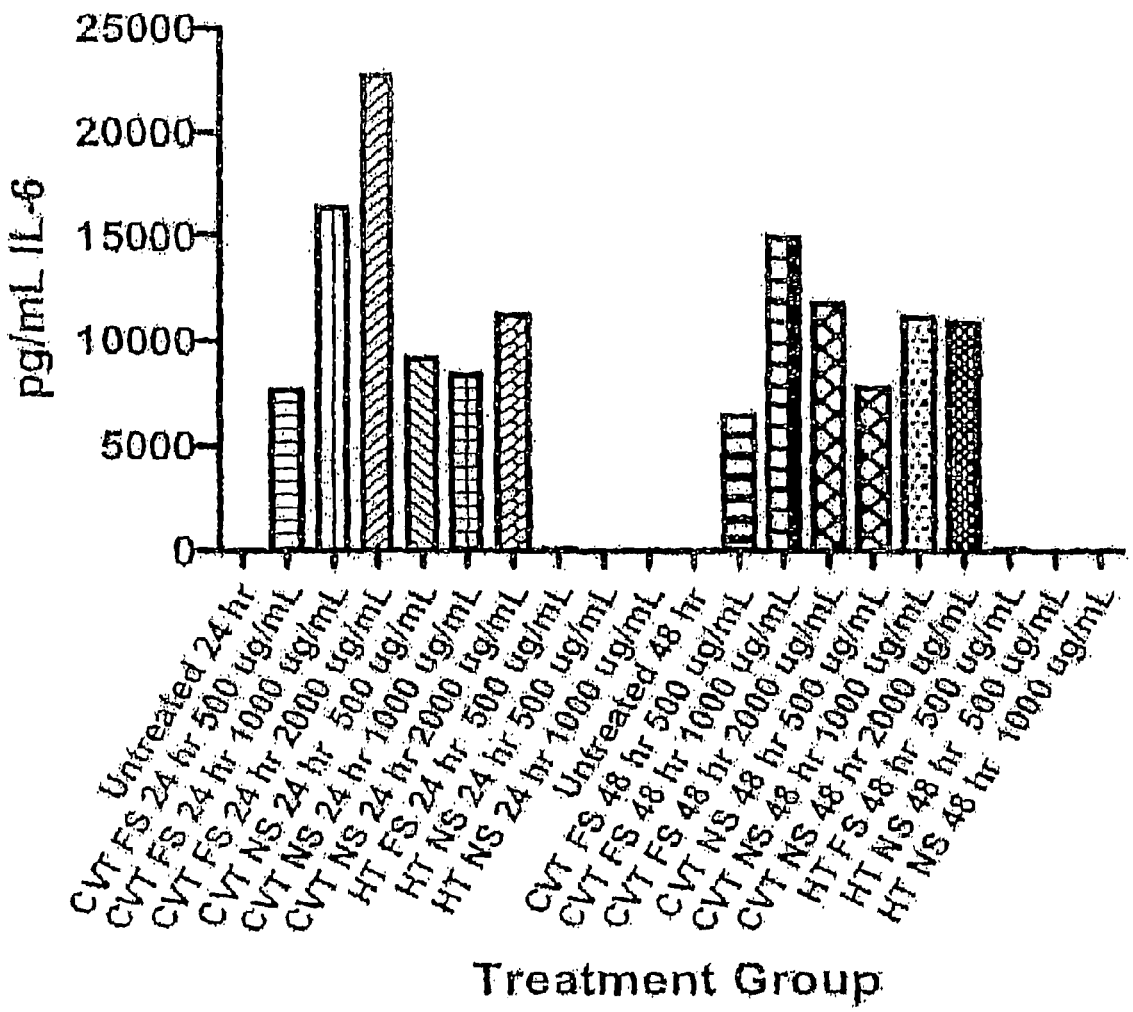
FIGS. 8A and 8B show that CVT-E002 treatment stimulates IL-6 (FIG. 8A) and IFN-β (FIG. 8B) production in RAW264.7 cells in vitro.
Figure 8B:
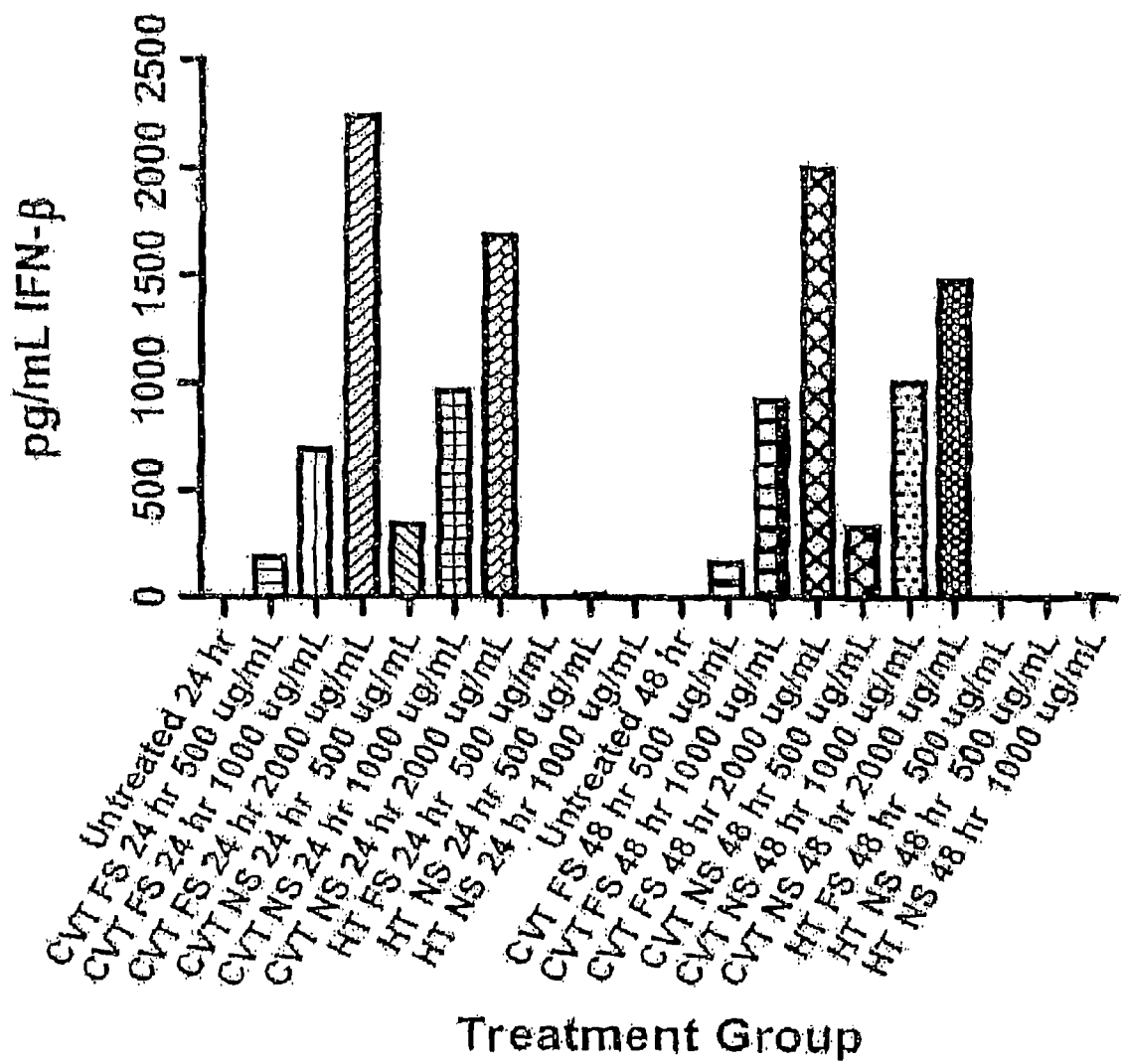
Figure 9:
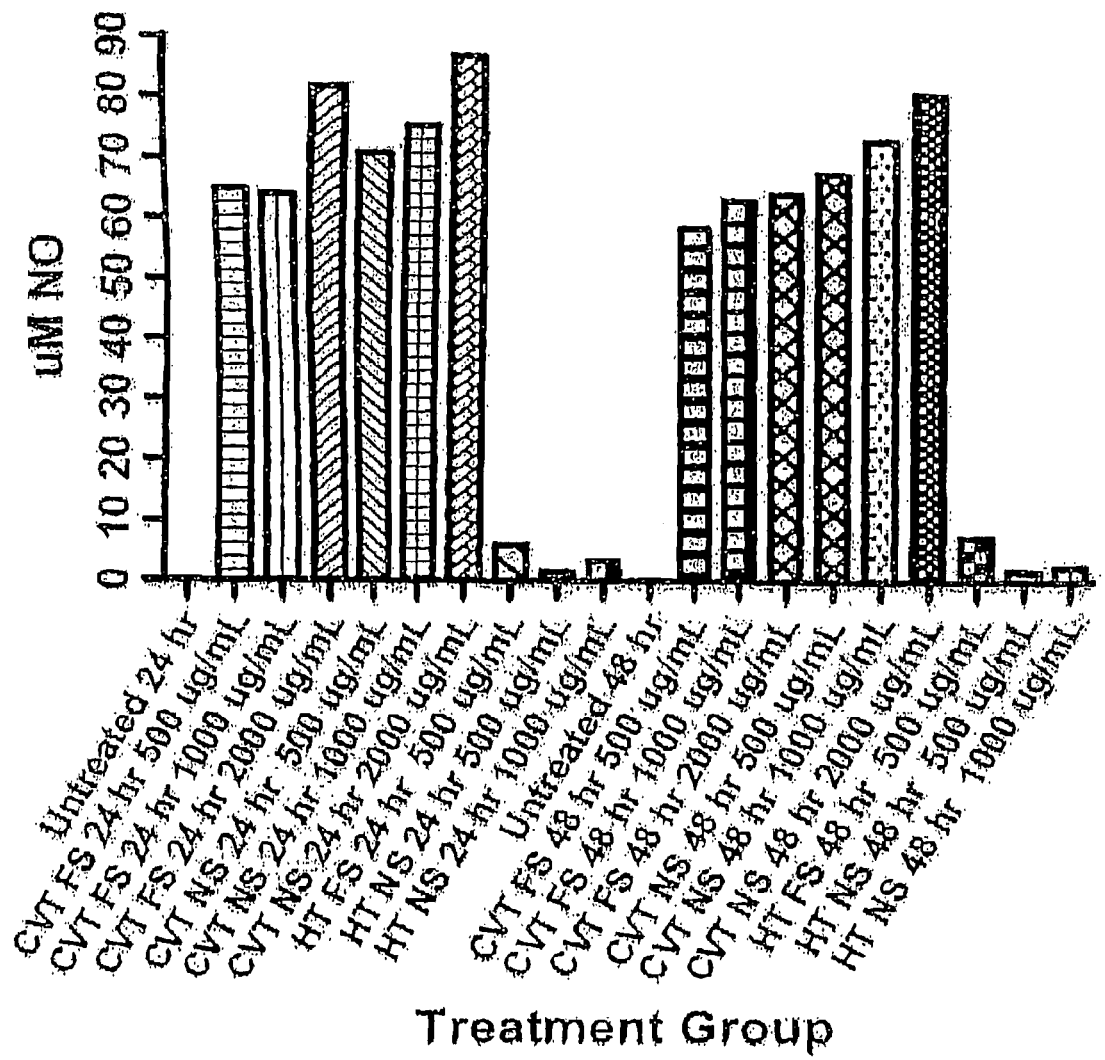
FIG. 9 shows that CVT-E002 treatment stimulates nitric oxide (NO) production in vitro.
Figure 10:
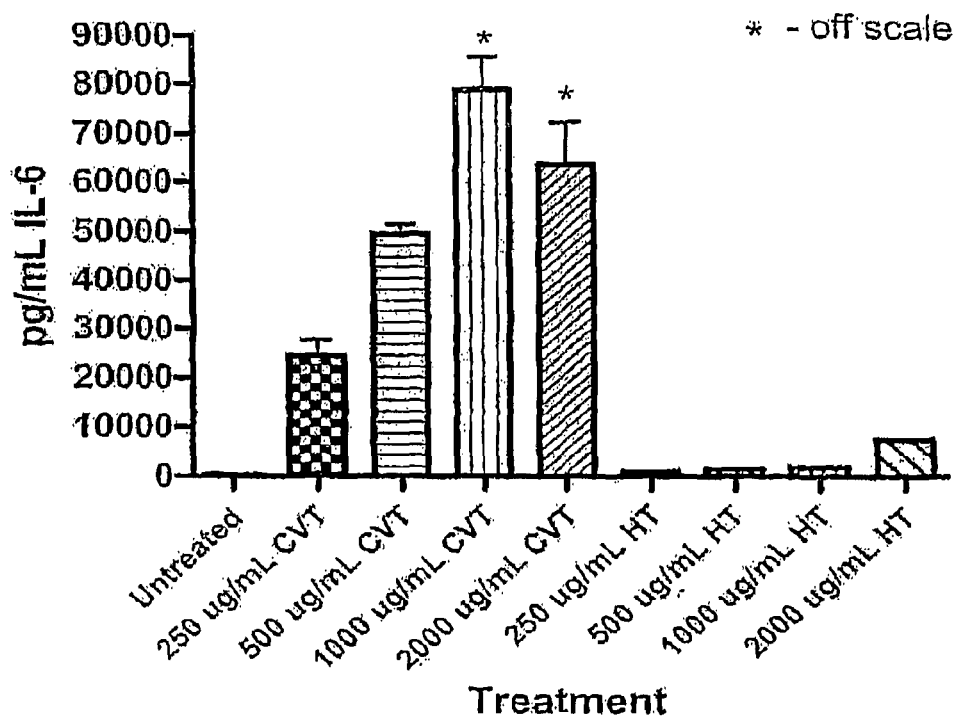
FIG. 10 shows IL-6 production by primary human monocyte/macrophages following incubation with CVT-E002.

CVT-E002 modulates the activity of the innate immune system to produce inflammatory and anti-viral factors. Treatment of murine monocytic cells in vitro with CVT-E002 and subsequent exposure to herpes simplex virus type 2 or vesicular stomatitis virus resulted in significantly elevated levels of IL-6, interferon-β and nitric oxide production in a dose-dependent manner, whereas untreated and control treated cultures were negative (Example 1, FIGS. 8A, 8B and 9). Similarly, incubation of primary human monocytes/macrophages with CVT-E002 for forty hours resulted in significant dose-dependent production of IL-6 (FIG. 10).

Figure 11:
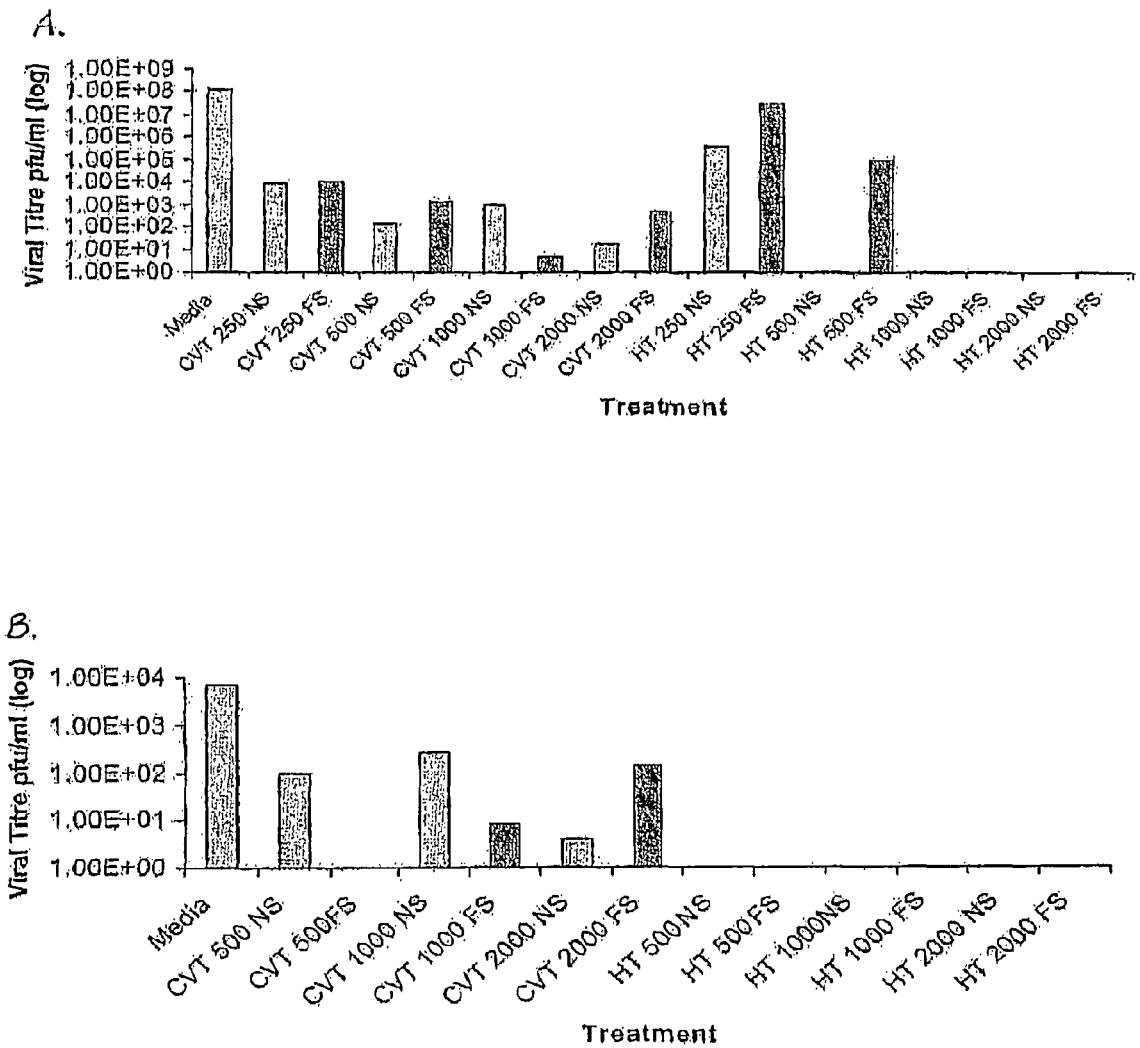
FIGS. 11A and 11B show that CVT-E002 significantly inhibits VSV replication in vitro.

Using vesicular stomatitis virus labelled with green fluorescent protein (VSV-GFP), CVT-E002 significantly inhibited virus replication in vitro (FIGS. 11A and 11B). CVT-E002 may protect against a variety of sexually transmitted viral infections, including HIV-1. The results described herein support topical application of CVT-E002 to rapidly activate the innate mucosal immune system and induce a local antiviral state which protects mucosal surfaces against infection with sexually-transmitted agents. This approach may be safer and less susceptible to selection of resistant pathogens since it would use more "natural microbicides" and the evolutionarily ancient innate mucosal immune responses for protection.

Signaling by all TLRs (except TLR3) occurs through the myeloid differentiation primary response gene 88 (MyD88), an adapter protein which activates the transcription factor NF-κB. To determine whether the cytokine responses following CVT-E002 treatment were dependent on MyD88 signaling, peritoneal macrophage cultures were established from C57Bl/6 wild-type or MyD88 knockout (MyD88−/−) mice and treated with or without CVT-E002 (Example 4). Production of both IL-6 and IFN-β following CVT-E002 treatment was MyD88-dependent, indicating that CVT-E002 activates the production of proinflammatory and anti-viral cytokines in immune cells based on stimulation of TLR signaling.

Figure 14:
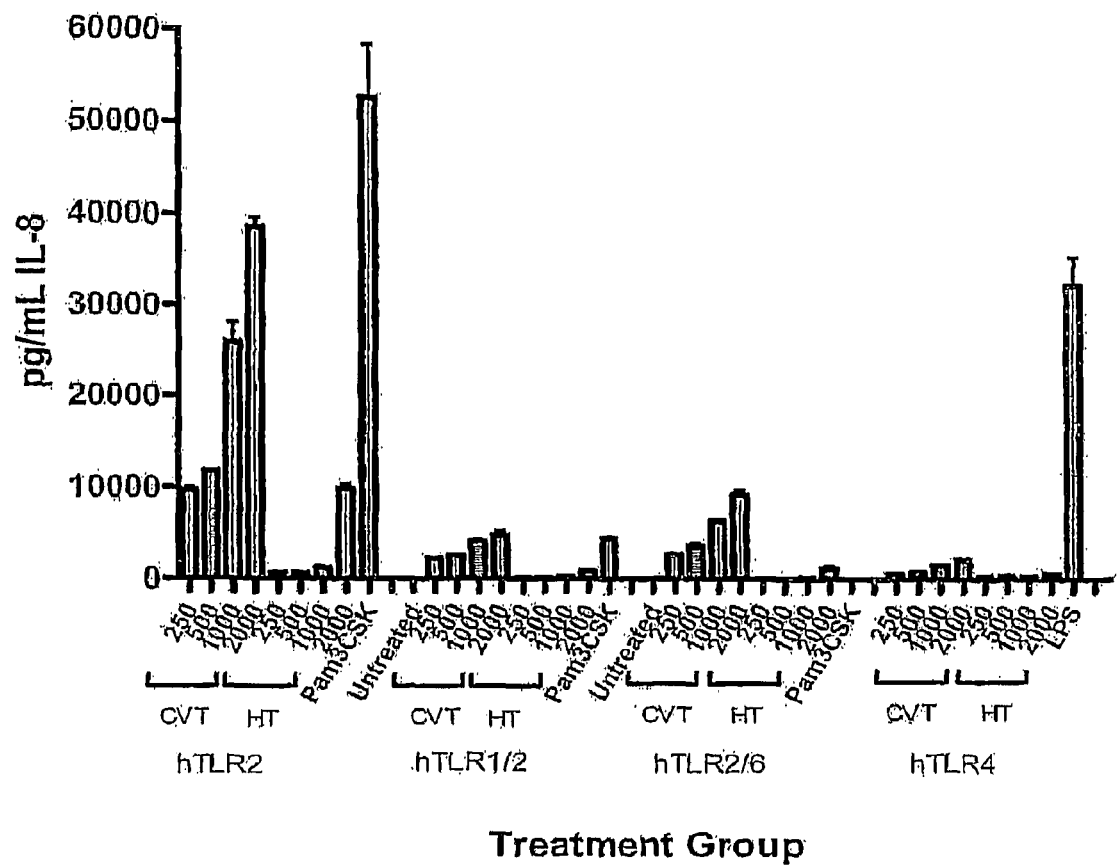
FIG. 14 shows that CVT-E002 treatment over a period of 24 hours stimulates IL-8 production in hTLR2, hTLR1/2, hTLR2/6 and hTLR4 transfected 293 cells (Pam3CSK/LPS Controls). hTLR4 represents co-expression of hTLR4 with MDR and CD14.
Figure 15:
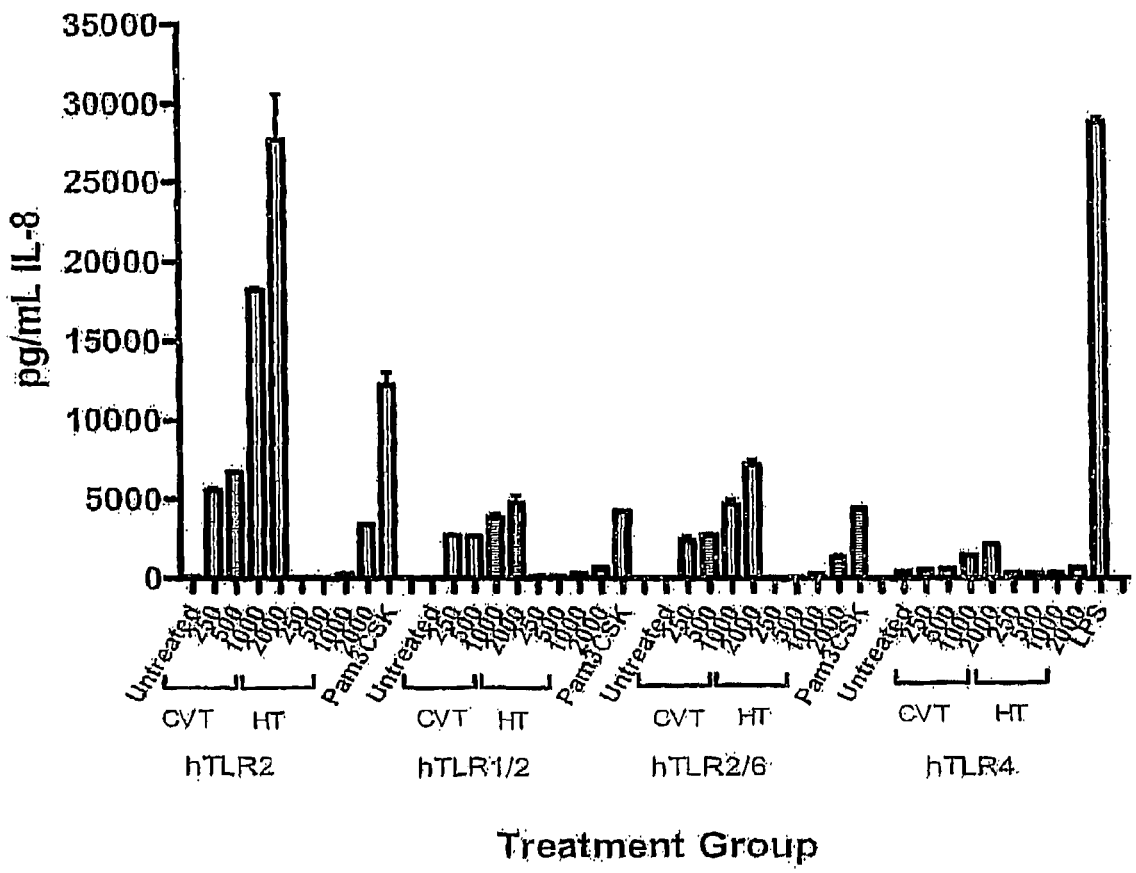
FIG. 15 shows that CVT-E002 treatment over a period of 48 hours stimulates IL-8 production in hTLR2, hTLR1/2, hTLR2/6 and hTLR4 transfected 293 cells (Pam3CSK/LPS Controls). hTLR4 represents co-expression of hTLR4 with MDR and CD14.

To determine which TLRs are activated by CVT-E002, HEK293 cells were utilized which were constructed to stably express specific human TLR genes (Example 5, FIGS. 14 and 15). Although CVT-E002 did not stimulate IL-8 production from cells expressing hTLR4 alone, the results show that CVT-E002 stimulated IL-8 production from cells expressing hTLR4 and MD2-CD14 in a dose-dependent manner at two different time points. Interestingly, CVT-E002 also stimulated cells expressing human TLR2 in a dose-dependent manner. Since TLR2 can also form heterodimers with TLR1 and TLR6, the stimulation of cells expressing hTLR2 alone or hTLR2/1 and hTLR2/6 was compared. Incubation with CVT-E002 resulted in dose-dependent IL-8 production in each of these cell lines, although cells expressing hTLR2 alone consistently produced significantly higher IL-8 levels. In experiments comparing all four lines with equivalent cell counts, the bulk of CVT's innate immune activation was via TLR2. Using cells expressing individual TLRs, it was found that CVT-E002 demonstrates a minimal signal via TLR4, which is the innate PRR for lipopolysaccharide (LPS) (FIG. 14). Overall, the results suggest that ginseng fractions (for example, CVT-E002) can activate the innate immune system via TLRs. This may account for their anti-infective protective effects and indicates that ginseng fractions may be useful as potential vaccine adjuvants to help stimulate innate and adaptive immunity against the vaccine ingredients, thereby making the vaccine more effective.

In view of the ability of CVT-E002 to activate the innate and/or adaptive immune responses to inhibit virus replication, the inventors have found that CVT-E002 is also useful in the prevention, treatment or amelioration of other conditions associated with activation of innate immunity signaling including, but not limited to, allergies and asthma.

Based on allergen/antigen in vitro models, a cell co-culture system incubating airway viruses with isolated human white blood cells has been developed using parainfluenza virus type I (PIV) and respiratory syncytial virus (RSV). These viruses were chosen because they are ssRNA airway viruses that frequently infect humans throughout their lives, and are associated with asthma exacerbations.

Figure 2:
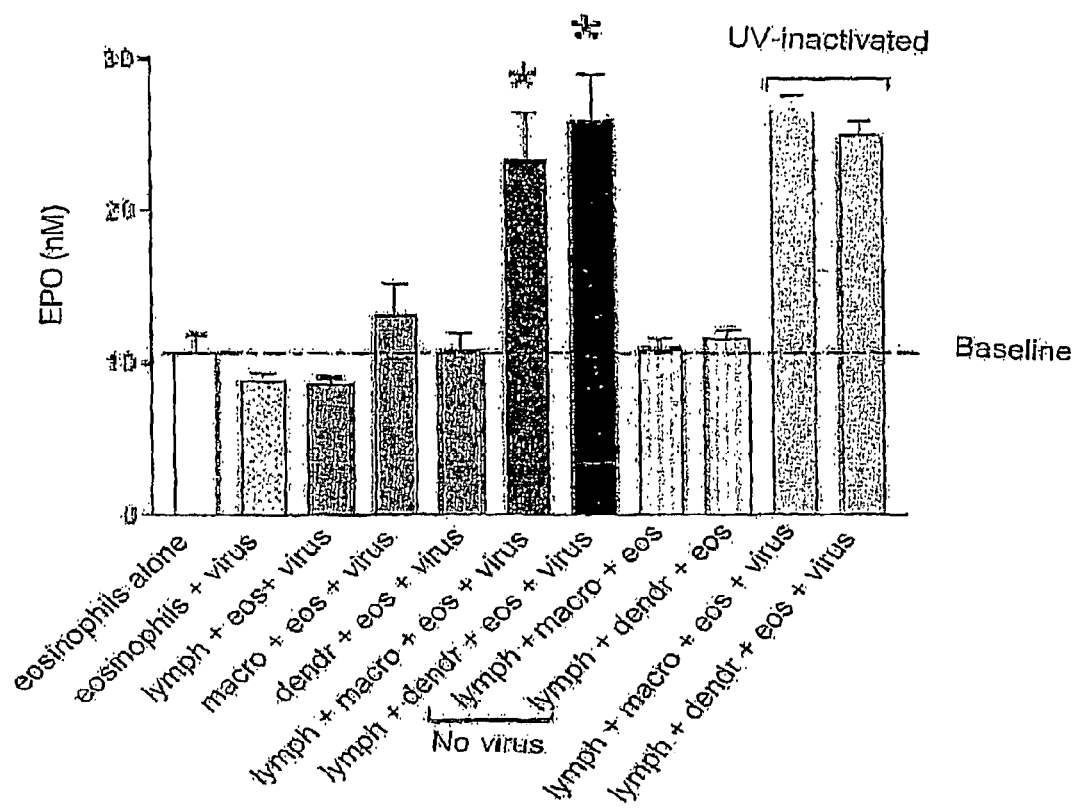
FIG. 2 shows eosinophil peroxidase release from human eosinophils after co-culture with parainfluenza virus and various combinations of autologous lymphocytes, dendritic cells, and macrophages (p<0.001). Each bar is the mean±SEM of at least twelve experiments using different donors.

As shown in FIG. 2, viruses in the presence of eosinophils do not directly induce release of eosinophil peroxidase (EPO). Rather, viruses induce release of EPO only when the eosinophils are incubated with particular combinations of lymphocytes, dendritic cells, and macrophages (i.e., the latter two being antigen presenting cells). Antigen presenting cells alone with virus and eosinophils do not induce EPO release. No EPO release occurs in any combination in the absence of virus. Thus, virus cultured with antigen presenting cells, appears to activate lymphocytes to induce EPO release from eosinophils. UV-inactivation of the virus does not prevent this effect.

Figure 3:
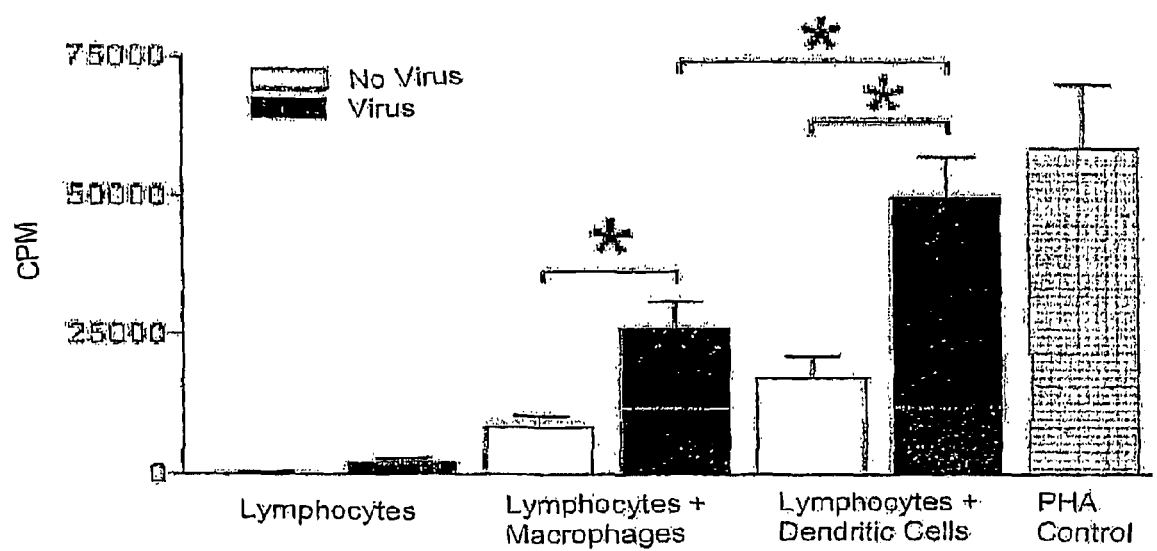
FIG. 3 shows that lymphocyte proliferation (as measured by $H^3$-thymidine incorporation) occurs after six days in culture (34° C., 5% $CO_2$) with parainfluenza virus and antigen-presenting cells (i.e., macrophages and dendritic cells). Each bar is the mean±SEM of at least five experiments using different donors for active virus. Similar results were obtained with RSV (data not shown).

EPO release was chosen as a measure of mediator release because of its importance in eosinophil function, its anti-viral properties, and experience in measuring it. When PIV or RSV are incubated with eosinophils alone, no EPO release is seen, suggesting direct eosinophil degranulation is not possible. Similar negative results were seen by others using rhinovirus. The leukocyte donors are adults with atopic background exhibiting peripheral blood eosinophilia. Since PIV and RSV are common infections, these donors would have immunity to this virus in the form of memory T-cells. In the present model, lymphocyte proliferation occurs in response to PIV and RSV but again only when co-cultured with antigen-presenting cells. As shown in FIG. 3, lymphocyte proliferation occurred after six days in culture with parainfluenza virus and antigen-presenting cells (i.e., macrophages and dendritic cells), with greater proliferation observed with dendritic cells compared to macrophages. Phytohemagglutinin (PHA, 5 µg/ml) with lymphocytes alone served as the positive control. Production of cytokines (IFN-γ and GMCSF) were found in this co-culture, though their source or relevance to the induction of EPO release has not been determined.

Similar to the results for virus stimulation, CVT-E002 cannot directly induce lymphocyte proliferation; however, a strong proliferative response is observed when CVT-E002 is cultured with dendritic cells (Examples 2 and 3). Lymphocyte proliferation occurs after six days in culture with lymphocytes, CVT-E002 and dendritic cells. There may be a slight increase in proliferation when CVT-E002 is added to the wells with virus. Using flow cytometry to characterize the cells, increased expression of HLA-DR in CVT-E002 stimulated dendritic cells was observed. The proliferating lymphocytes were CD4 positive and demonstrated increased expression of activation marker CD25. LPS stimulation served as the positive control. Without CVT-E002 or virus, neither proliferation nor CD25 up regulation was observed from co-culture of dendritic cells with lymphocytes. CVT-E002 stimulation induced increased expression of CD25 from CD4+ lymphocytes similar to that seen in virus infection alone. The combination further augmented expression.

Atopic/allergic asthma is a Th2 disease. CVT-E002 is capable of producing Th1 responses (example 2, FIG. 5) and this Th1 bias has the potential to inhibit the Th2 response and thus be used as a therapeutic for atopic/allergic diseases. In a widely used model of atopic/allergic asthma, whereby mice were sensitized with i.p OVA and alum and then challenged with OVA to initiate allergic disease in the airways CVT-E002 was able to prevent the development of AHR and decrease the amount of eosinophilic airway inflammation (Example 7, FIGS. 16a and 16b). In the control non-sensitized animals no atopic/allergic disease was present whereas mice that were sensitized, given saline by gavage, and then challenged with OVA developed a robust atopic/allergic disease in the airways consisting of eosinophilic airway inflammation and AHR. In test mice sensitized to OVA, given CVT-E002 by gavage, and then challenged with OVA both eosinophilic airway inflammation and AHR to inhaled methacholine were inhibited.

CVT-E002 may be useful in the treatment of asthma which is caused by either respiratory viral infections or other irritants and triggers. While most adults will be exposed to the same common virus infections every year, a subset of patients with asthma will react with decreased lung function. The properties of CVT-E002 may be beneficial to such patients. As described herein and in the Examples, CVT-E002 may be useful in modulating the response to virus infection in asthma patients by inhibiting virus replication and/or by favoring a Th1 immune response. Inhibition of virus replication is beneficial, as it lowers the degree of inflammation and subsequent airway obstruction. Promotion of a Th1 immune response is beneficial as it counteracts the Th2 response involved in Atopic reactions.

In addition to treatment of asthma due to respiratory viral infections, CVT-E002 may also be effective for the treatment of asthma caused by other irritants and triggers. Such irritants and triggers include, but are not limited to, indoor allergens such as domestic mites, furred animals, cockroaches and fungi; outdoor allergens such as pollen and molds; indoor air pollutants such as cigarette smoke; outdoor air pollutants such as ozone, nitrogen oxides, acidic aerosols and particulates; occupational exposures; food and food additives; drugs such as aspirin and non-steroidal anti-inflammatory drugs and beta-blockers; rhinitis; sinusitis; polyposis; gastroesophageal reflux; hormonal fluctuations; dry cold air; and exercise.

The immunomodulatory properties of CVT-E002 may also be beneficial to patients, since CVT-E002 enhances the release of cytokines, the interferons from lymphocytes and/or dendritic cells and is involved in the interaction of lymphocytes and antigen presenting cells.

In the above description and following examples it is to be understood that the mention of the preferred embodiment of CVT-E002 is exemplary only and the described utility in activities would be appropriate to all ginseng fractions have the desired activity.

The invention will now be further elucidated by the following Examples.

Example 1

Effect of CVT-E002 on Virus Replication In Vitro

The ability of various doses of CVT-E002 to inhibit virus replication in murine monocytic cells in vitro was investigated. Various doses (0, 10, 100 and 500 µg/ml) of CVT-E002 and HT-1001 (an exemplary ginseng fraction comprising ginsenosides Rb1 and Rg1 and described in U.S. Pat. No. 6,083,932) as control (250-2000 µg) were dissolved in PBS buffer and diluted to final concentrations in complete tissue culture medium and added to RAW-264 murine macrophage cells at 37° C. in vitro. Following treatment of the cells for 24 or 48 hours, treated and untreated cell cultures were exposed to herpes simplex virus type 2 (HSV-2) or vesicular stomatitis virus (VSV). Virus replication was assessed using plaque assays. Supernatants of CVT-E002 and control cultures were collected at various times following treatment and assessed for type I IFNs, TNFα, IL-6 and nitric oxide (NO) using ELISA. Significantly elevated levels of IL-6 (FIG. 8A), IFNβ (FIG. 8B) and NO (FIG. 9) were produced by RAW cells following treatment with CVT-E002 in a dose dependent manner. Untreated and control treated cultures were negative. Data on cytokine production and viral titer were examined for correlations.

CVT-E002 was also tested for stimulation of TNFα and IFNα. TNFα was elevated in both CVT-E002 and HT-1001 treated groups. Results of IFNα were unreliable, possibly due to a poor ELISA (data not shown). Importantly, incubation of primary human monocyte/macrophage cultures with CVT-E002 resulted in significant dose-dependent production of IL-6 (FIG. 10). VSV genetically engineered to express green fluorescent protein (VSV-GFP) was also utilized to show that CVT-E002 significantly inhibited virus replication in vitro (FIGS. 11A and 11B).

Example 2

Mechanism by which Anti-Viral Activity is Induced by CVT-E002

Figure 4:
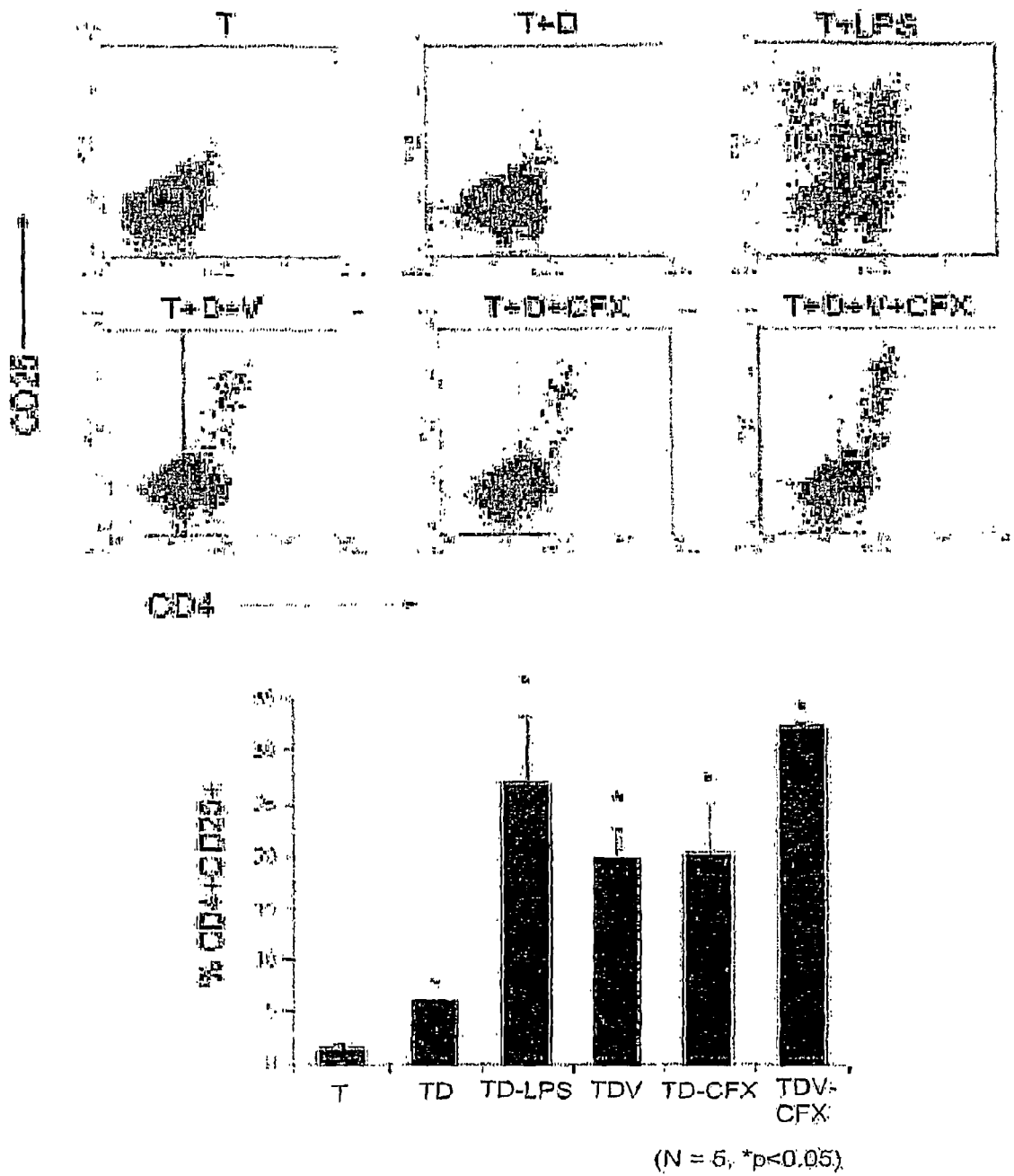
FIG. 4 shows the results of flow cytometry to characterize lymphocytes in co-culture with dendritic cells.
Figure 5:
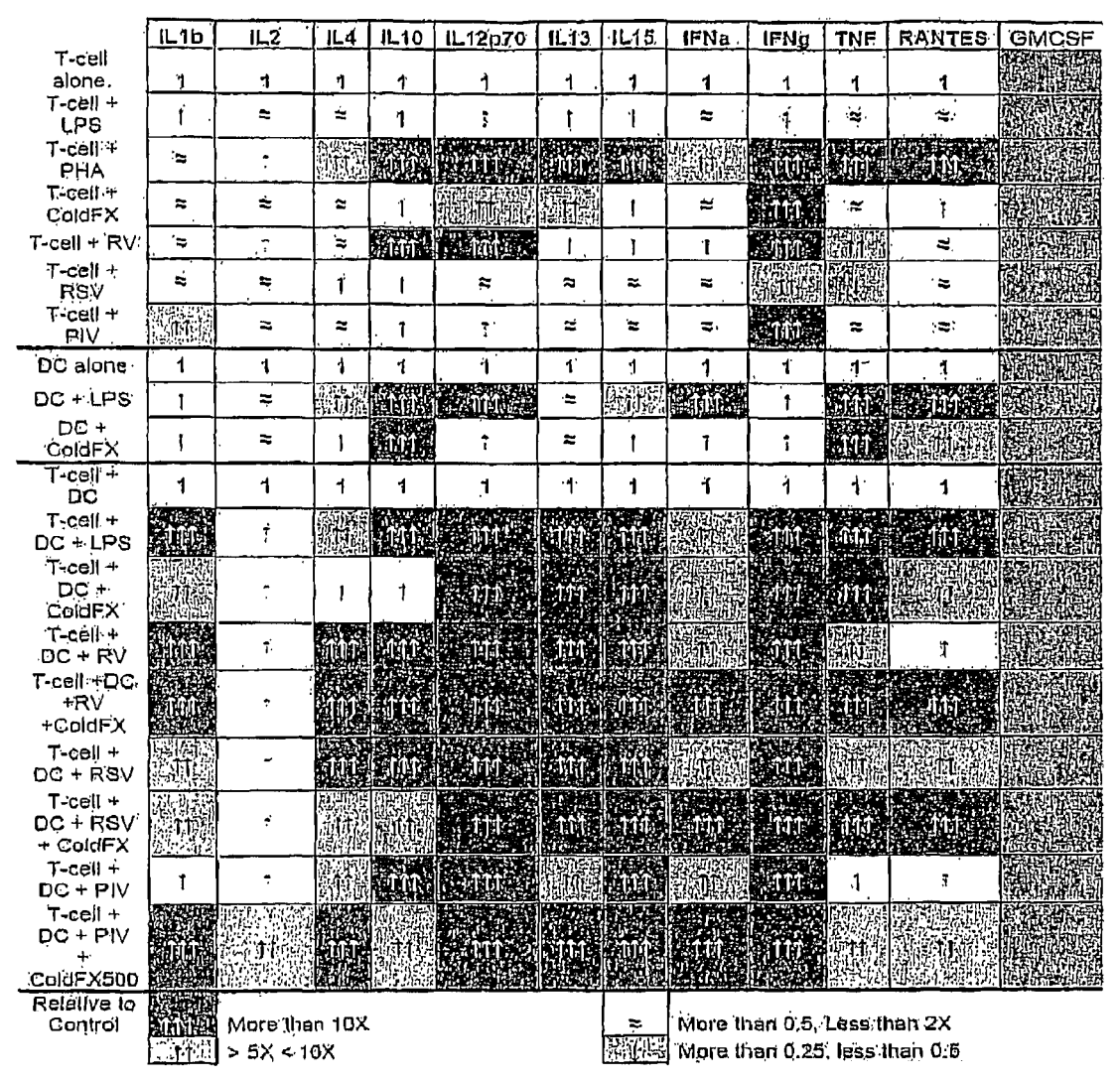
Figure 6:
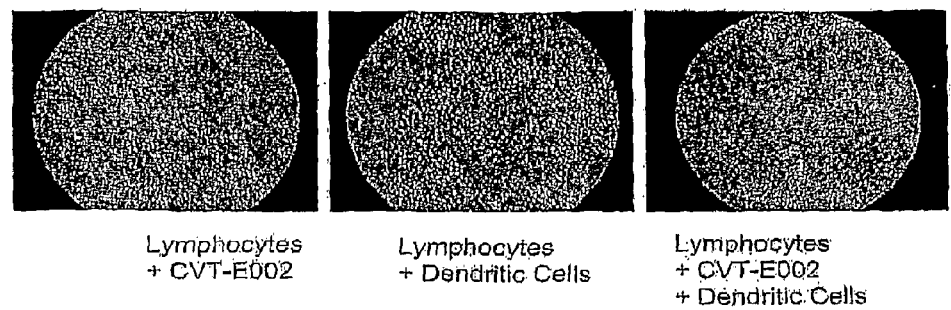
FIG. 6 shows that lymphocyte proliferation (as visualized by light microscopy and measure by $H^3$-thymine incorporation) occurs after six days in culture (34° C., 5% $CO_2$) with lymphocytes, CVT-E002 and dendritic cells.
Figure 6:
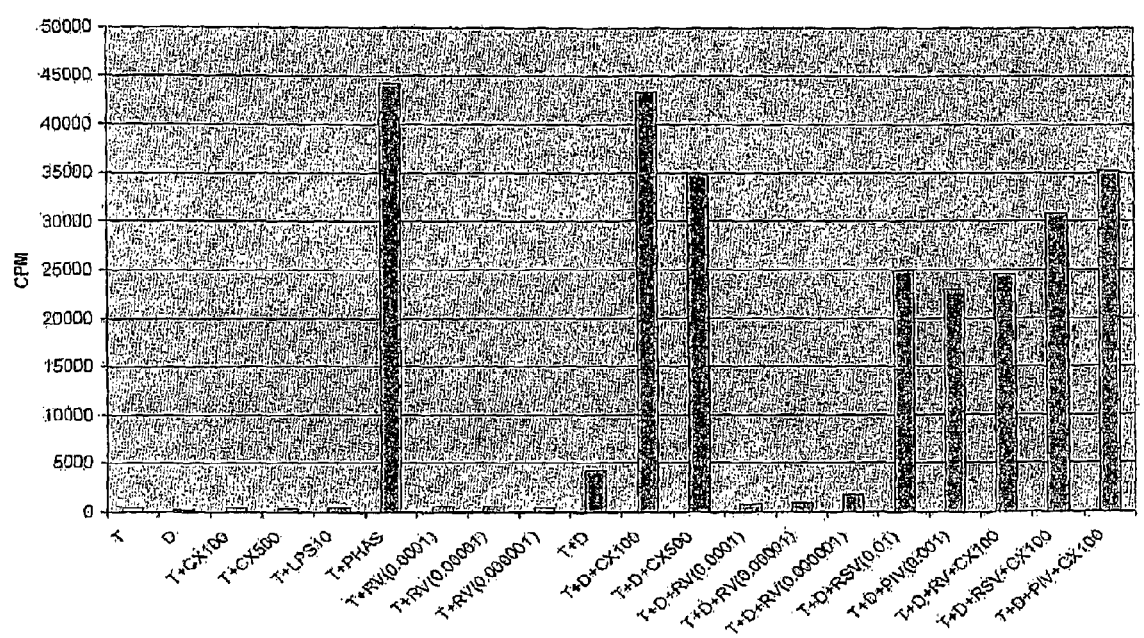

Dendritic cells (DCs) were co-cultured with lymphocytes and flowcytometry was used to characterize the lymphocytes. LPS stimulation was used as a positive control. RSV and PIV were found to induce proliferation of CD3+CD4+CD25+ T cells in the presence of dendritic cells (DCs) (FIG. 4, n=3 each). Compared to uninfected DCs cultured with lymphocytes, RSV induces production of interferons α and γ, TNF α, RANTES, IL-1, 2, 4, 10, 12, 13, and 15 (FIG. 5, n=1). The data are represented in relation to respective uninfected controls (given a value of 1). CVT-E002 with T cells alone induced release of IFNγ and IL12. CVT-E002 with DCs alone induced release of TNF, IFNγ, IL-1, 10, 12, and 15. Adding CVT-E002 to the cell culture with virus greatly augmented the cytokine/chemokine release. In addition, compared to uninfected cells, CVT-E002 could induce lymphocyte proliferation in the presence of DCs without virus (FIG. 6).

Example 3

Effect of CVT-E002 on Dendritic Cell Function

Dendritic cells (DCs) were derived from blood monocytes by treatment with GM-CSF and IL-4 for seven days. DCs were incubated in the presence or absence of 5 mg/ml self-quenched DQ-Ovalbumin (DQ-OVA) and CVT-E002. DQ-OVA is a fluorescent dye attached to ovalbumin. DQ-OVA's fluorescence is quenched as an intact molecule, but when degraded through antigen presentation by DCs, the fluorescent dye is released and emission is allowed.

Figure 7A:
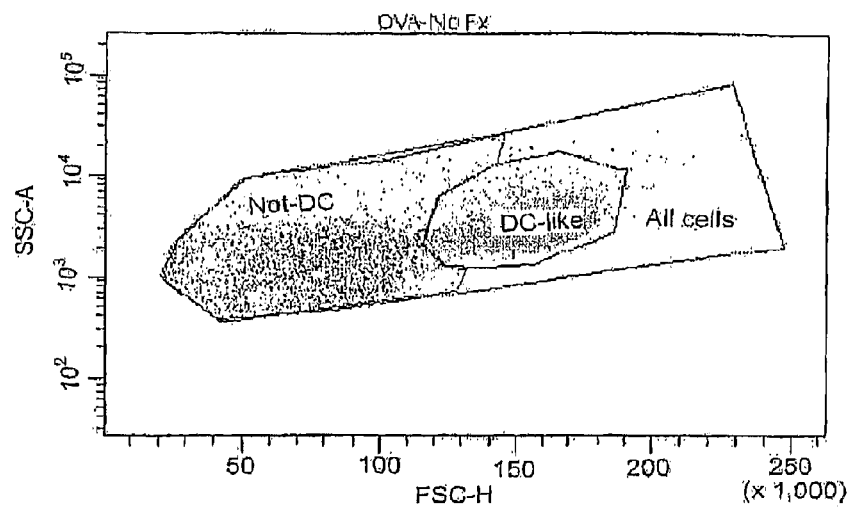
FIGS. 7A-D show results of flow cytometry analysis of antigen presentation and DC maturation.

FIG. 7A shows the subpopulations of cells. "DC-like" cells are consistent by size and granularity with mature dendritic cells while "Not DC" are immature DC as well as differentiation-refractant monocytes and T-cells. LPS-treated cells were used as a positive control for DC maturation. Using flow cytometry to determine size and granularity, there appeared to be a subpopulation of monocytes, which are believed to represent an immature phenotype (Not-DC) as compared to the mature DC (DC-like). This impression is based on previous experience of staining with CD11c and HLA-DR (data not shown).

Figure 7B:
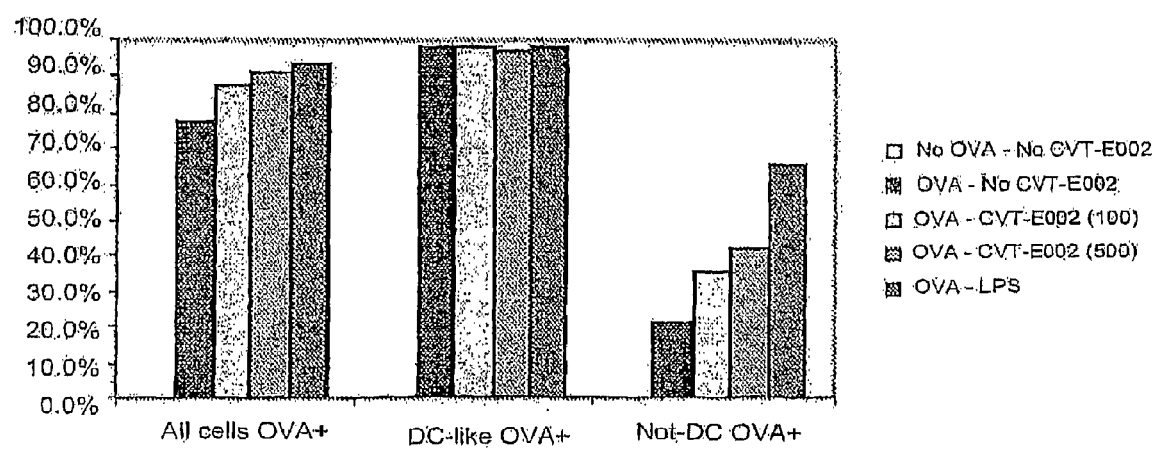

The DCs incorporated DQ-OVA as exhibited by fluorescence (FIG. 7B). Interestingly, CVT-E002 enhanced the overall DQ-OVA signal in a dose-dependent manner (All cells OVA+). While the DC-like population is 100% OVA-positive, the immature population appears to take up the ovalbumin better after CVT-E002 (Not-DC OVA+, FIG. 7B).

Figure 7C:
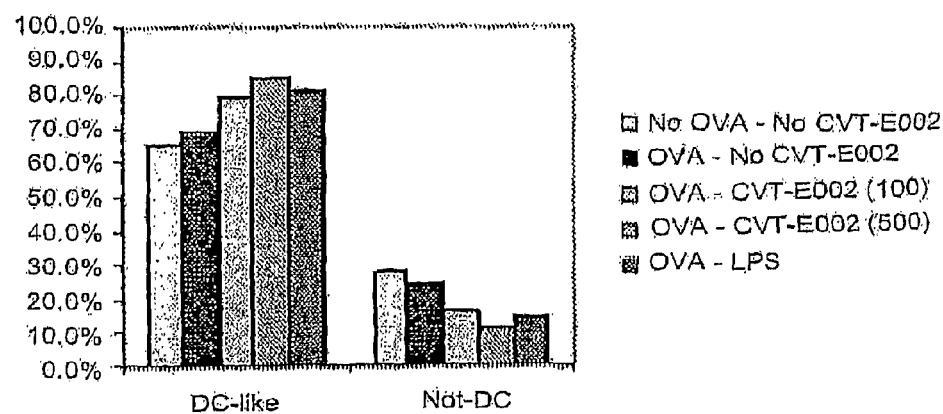
Figure 7D:
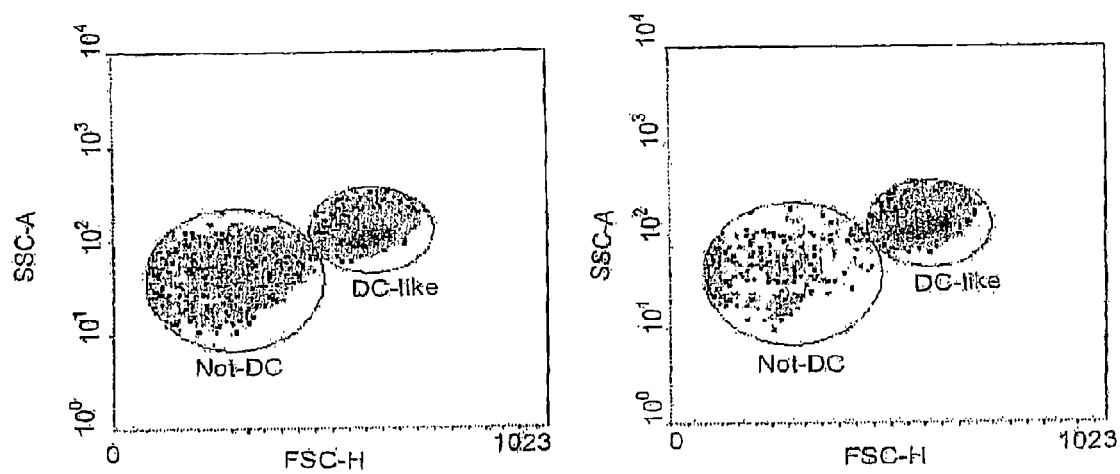

CVT-E002 treatment shifts the number of monocytes from the Not-DC population to the mature DC-like (mature DC pool) (FIGS. 7C and 7D). Preliminary phenotyping of these populations with CD11c and MHC II staining confirms our impression of maturity versus immaturity. These data suggest that CVT-E002 improves DC function and maturity in addition to the DC cytokine data.

Example 4

Ability of CVT-E002 to Activate Nuclear Factor Kappa B (NF-κB) and to Signal Via MyD88

To determine whether CVT-E002 activates innate immune responses via interaction with TLRs, the abilities of CVT- E002 to activate NF-κB and to signal via MyD88 were examined. Peritoneal macrophages were isolated from normal mice (C57Bl/6 wild-type) and mice lacking MyD88 (i.e., MyD88 knock-out mice designated as "MyD88-/-").

Following 24 hours of incubation in vitro to permit attachment to the culture plates, the macrophages were washed, treated with various doses of CVT-E002 or FIT-1001, and incubated for a further 24 hours. HT-1001 was used as a control. The supernatants were collected and assessed for production of IL-1, IL-6, IFNβ and NO using ELISA. CpG DNA (MyD88-dependent) and dsRNA (a MyD88-independent ligand for TLR3) were included as positive and negative controls, respectively. Additionally, plasmids were constructed with the NF-κB promoter driving a reporter gene, LacZ. Cells transfected with this plasmid were treated with various doses of CVT-E002 and assessed for production of the reporter gene product.

Figure 12:
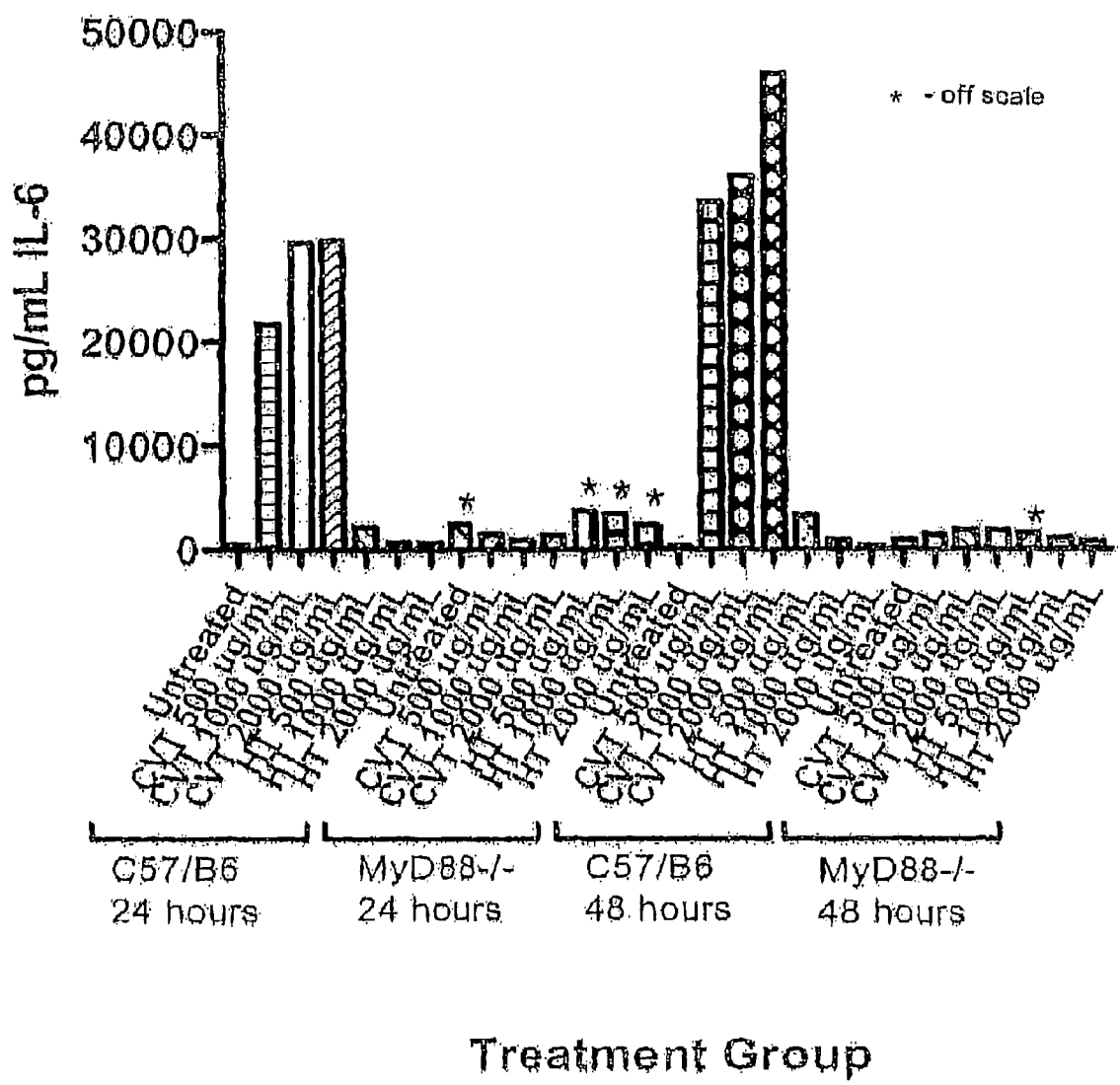
FIG. 12 shows IL-6 production during CVT-E002 or HT-1001 treatment of C57/B6 and MyD88–/– peritoneal macrophages.
Figure 13A:
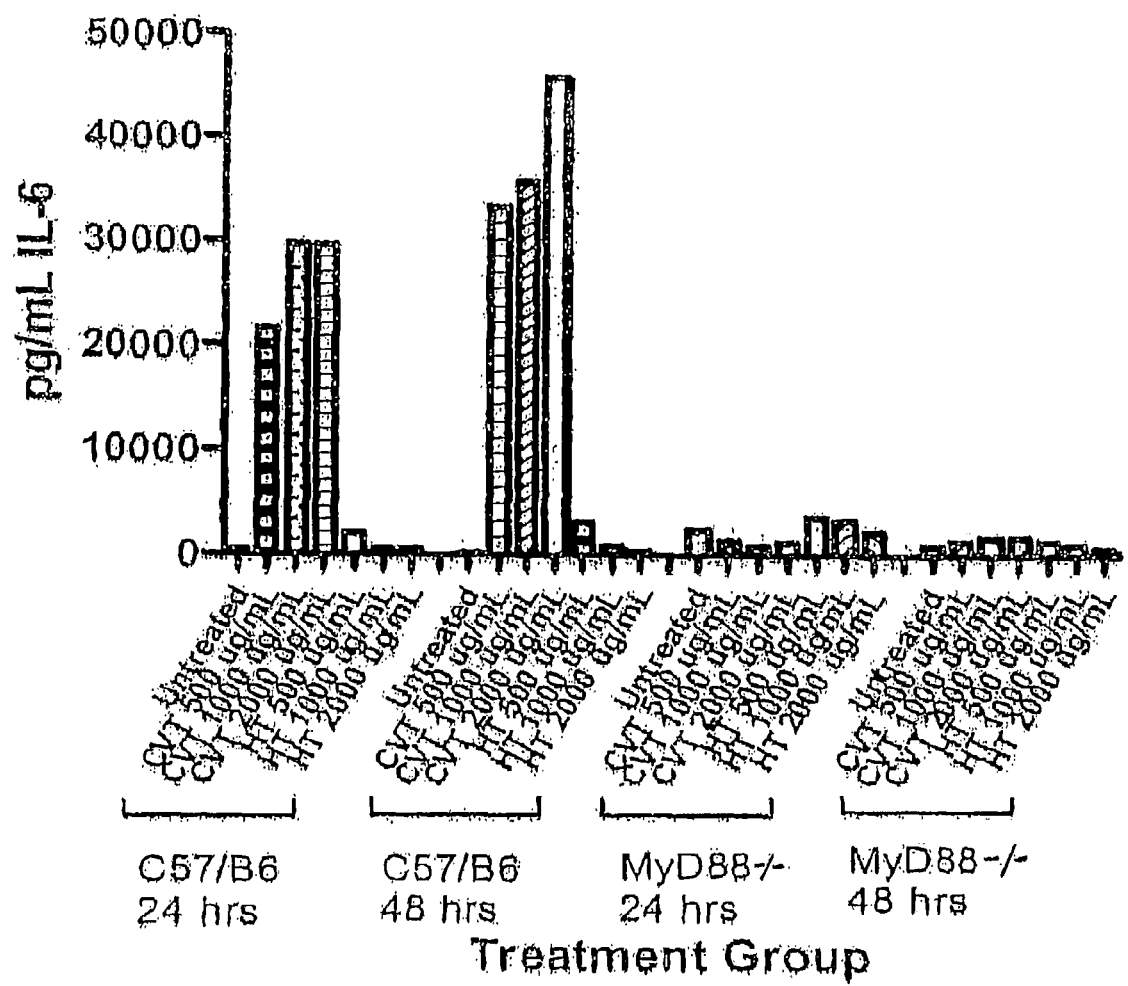
FIGS. 13A and 13B show IL-6 (FIG. 13A) or IFN-β (FIG. 13B) production during CVT-E002 or HT-1001 treatment of C57/B6 and MyD88–/– peritoneal macrophages.
Figure 13B:
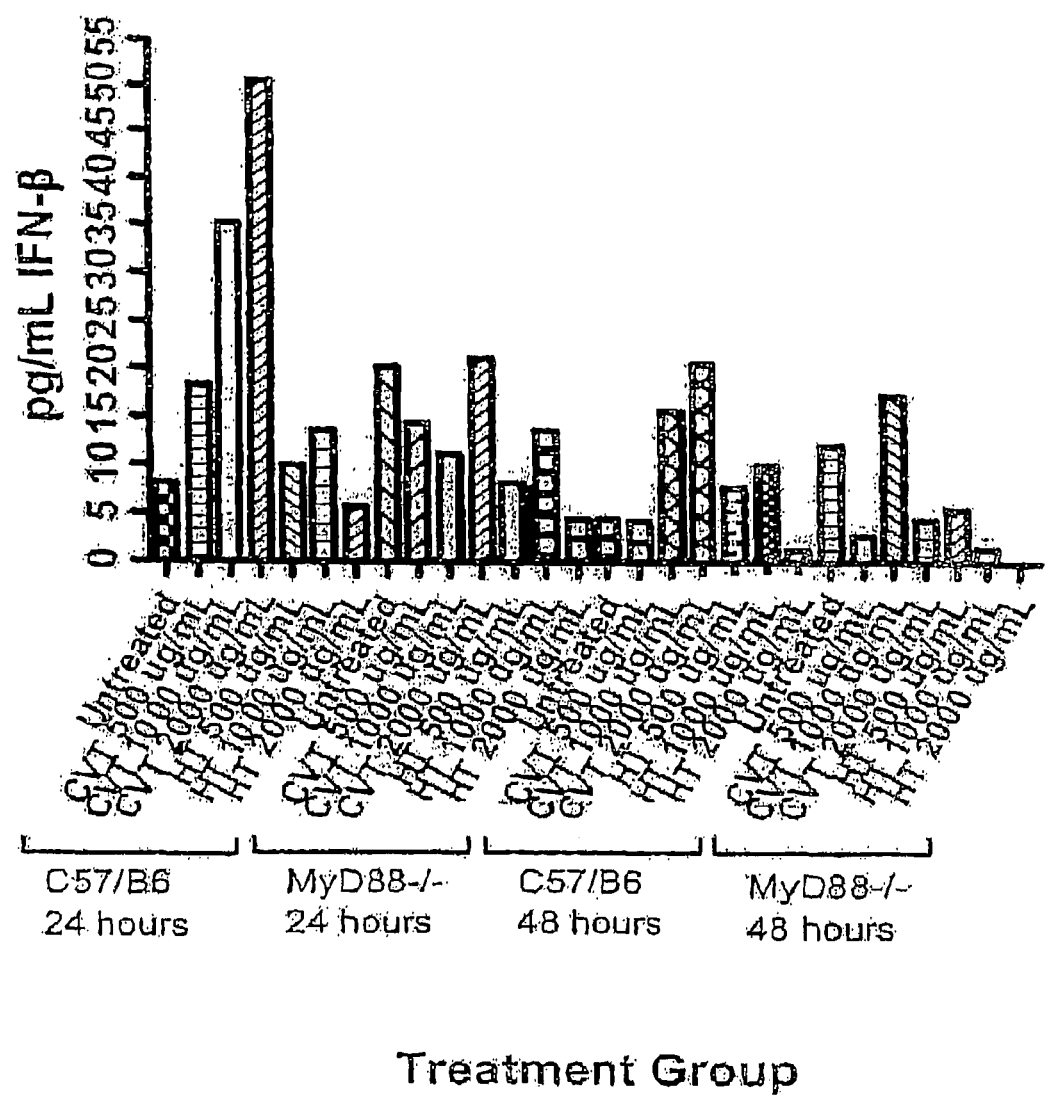

The results demonstrate that CVT-E002 induced significant levels of proinflammatory cytokine IL-6 and the antiviral factor type I IFN production in peritoneal macrophages from only wild-type, but not MyD88-/- mice (FIGS. 12, 13A and 13B). Untreated or HT-1001-treated cultures were negative. These results show that the CVT-E002-induced stimulation of IL-6 and IFNβ is MyD88-dependent, and indicate that CVT-E002 activates the production of proinflammatory and anti-viral cytokines in vertebrate immune cells via TLRs.

Example 5

Identification of TLR Utilized by CVT-E002

To identify the TLRs which may be receptors for CVT-E002, cells were constructed to express only individual TLR receptors. These cells were treated in vitro with optimal doses of CVT-E002 and control TLR ligands/agonists, and the supernatants of these cells were used to measure production of IL-1, IL-6, TNFα and NO. To ensure that cells expressing each individual TLR were functional, positive controls were included using known ligands/agonists for each TLR. The results indicate that CVT-E002 does not signal via TLR4 alone. CVT-E002 treatment for 24 hours stimulated IL-8 production in hTLR2, hTLR1/2, hTLR2/6 and hTLR4 transfected 293 cells (Pam3CSK/LPS Controls) (FIG. 14). CVT-E002 treatment for 48 hours stimulated IL-8 production in hTLR2, hTLR1/2, hTLR2/6 and hTLR4 transected 293 cells (Pam3CSK/LPS Controls) (FIG. 15). hTLR4 represents coexpression of hTLR4 with MDR and CD14. For both time periods, significant increases in IL-8 production were seen for all receptors.

Example 6

Effect of Mucosal Delivery of CVT-E002

Figure 17A:
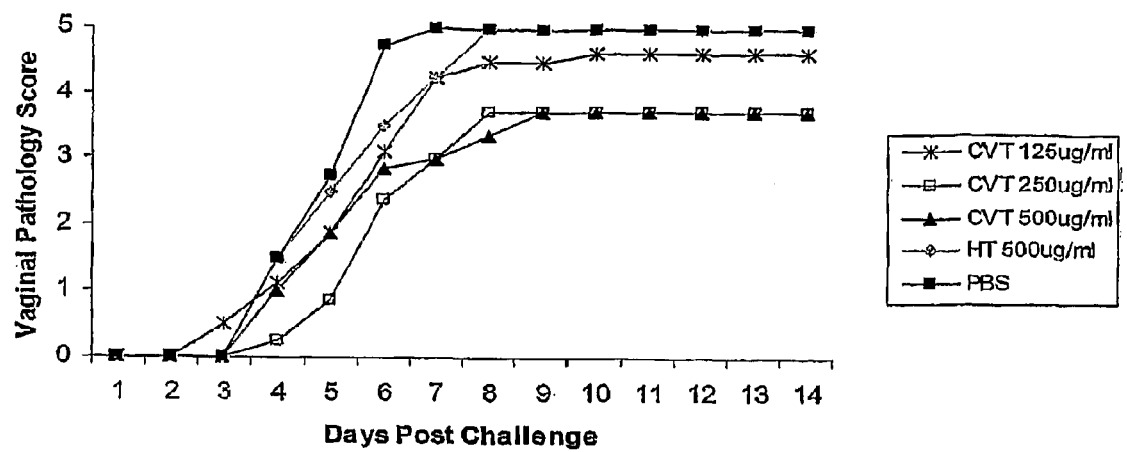
FIGS. 17A and B demonstrates that delivery of CVT-E002 to mucosal interfaces offers protection from a virus (HSV-2) delivered to the same mucosal surfaces.
Figure 17B:
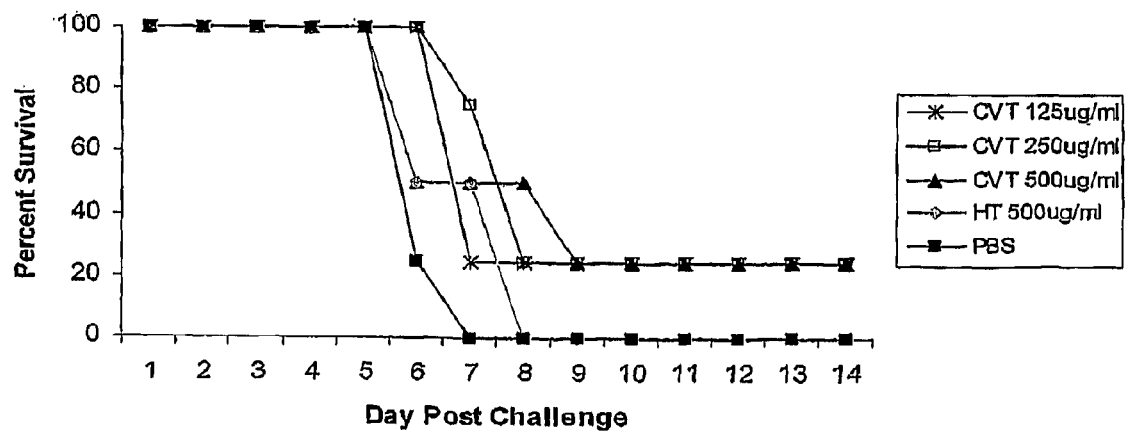
FIG. 17B percent survival of C57BL/6 mice given CVT-E002, HT1001 or PBS WAG following HSV-2 WAG challenge.

CVT-E002 or controls were delivered to mice orally in their diet, intransally or intravaginally. The mice were subsequently challenged intransally or intravaginally with various doses of HSV-2 or interferon-sensitive vesicular stomatitis virus (VSV). Protection against viral infection was assessed by measuring body weight, monitoring gross pathology, and measuring titers of challenge viruses in lung and genital washes and tissues using plaque assays at various time points following virus challenge (days 1-3 and 6 days after infection) (FIGS. 17A and 17B).

Example 7

Figure 16A:
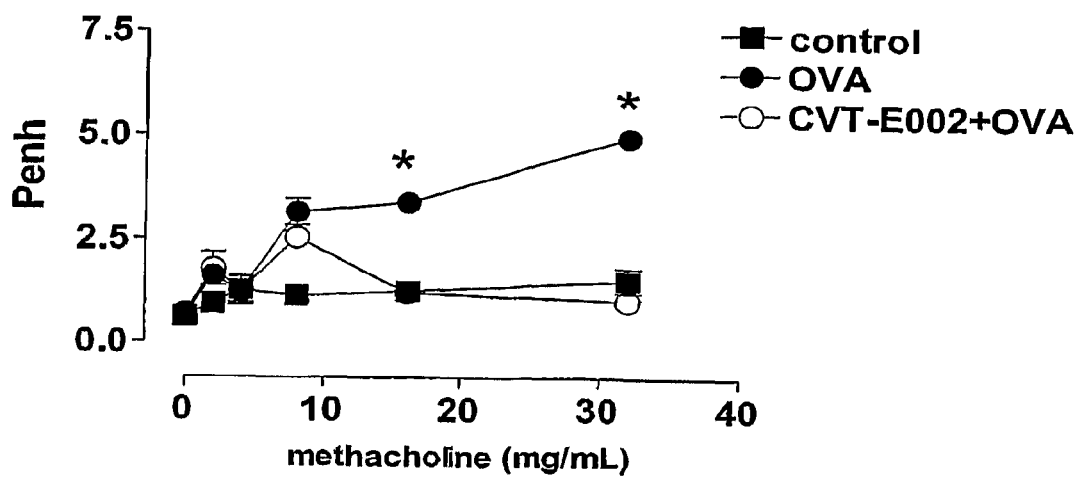
FIGS. 16A and 16B show that CVT-E002 treatment inhibits the development of airway hyperresponsiveness (AHR) (FIG. 16A) and decreases the amount of eosinophilic airway inflammation (FIG. 16B).
Figure 16B:
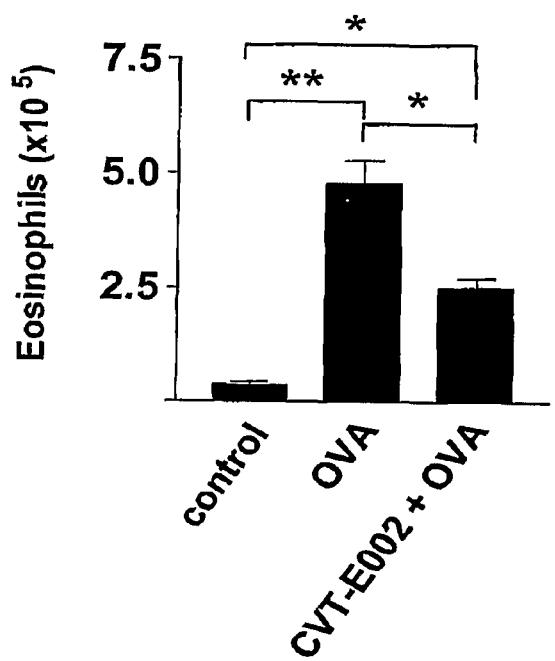

Ability of CVT-E002 to Inhibit the Development of Airway Hyperresponsiveness (AHR) and to Decrease the Amount of Eosinophilic Airway Inflammation OVA and CVT-E002+OVA mice were sensitized twice with OVA and alum i.p. injections while control animals received no immunization. Seven days following the final immunizations, control animals and CVT-E002+OVA mice received 200 mg/kg of CVT-E002 compound by gavage for seven consecutive days. 24 hours following the final gavage, all mice were challenged twice i.n. with 50 μg OVA and assessed for AHR and airway inflammation 24 h after the second challenge. Enhanced pause (Penh) was measured by whole-body plethysmography to determine AHR in response to methacholine challenge (n=3)*P<0.05 compared with OVA or control groups (FIG. 16A). Airway inflammation was determined by the number of eosinophils in BAL fluid (n=3). *P<0.05 compared with OVA or control groups (FIG. 16B).

As will be apparent to those skilled in the art, various modifications, adaptations and variations of the foregoing specific disclosure can be made without departing from the scope of the invention claimed herein.

The invention claimed is:

1. A method of treating or ameliorating airway hyperresponsiveness in a subject in need thereof comprising administering to the subject an effective amount of at least one ginseng fraction, wherein the ginseng fraction is selected from the group consisting of CVT-E002, $PQ_2$ and $PQ_{223}$.

2. The method according to claim 1, wherein the subject has asthma.

3. The method according to claim 1, wherein the subject has an allergy.

4. The method according to claim 1, wherein the ginseng fraction is CVT-E002.

5. The method according to claim 1, wherein the ginseng fraction modulates signal transduction from a Toll-like Receptor.

6. The method according to claim 5, wherein the Toll-like receptor is Toll-like receptor 2.

7. The method according to claim 5, wherein the Toll-like receptor is a heterodimer of Toll-like receptor 2 and Toll-like receptor 6.

8. The method according to claim 5, wherein the Toll-like receptor is a heterodimer of Toll-like receptor 2 and Toll-like receptor 1.

9. The method according to claim 5, wherein the Toll-like receptor is Toll-like receptor 4.

10. The method according to claim 1, wherein the ginseng fraction is administered in combination with another medicament, with one or more pharmaceutically acceptable carriers or with one or more food items.

* * * * *